US009382346B2

(12) United States Patent
Boyes et al.

(10) Patent No.: US 9,382,346 B2
(45) Date of Patent: Jul. 5, 2016

(54) GOLD NANOPARTICLE CONJUGATES AND USES THEREOF

(71) Applicant: Colorado School of Mines, Golden, CO (US)

(72) Inventors: Stephen G. Boyes, Denver, CO (US); Misty D. Rowe, Golden, CO (US); Jay Hotchkiss, Denver, CO (US)

(73) Assignee: COLORADO SCHOOL OF MINES, Golden, CO (US)

( * ) Notice: Subject to any disclaimer, the term of this patent is extended or adjusted under 35 U.S.C. 154(b) by 0 days.

(21) Appl. No.: 14/867,165

(22) Filed: Sep. 28, 2015

(65) Prior Publication Data

US 2016/0017065 A1 Jan. 21, 2016

Related U.S. Application Data

(62) Division of application No. 12/197,044, filed on Aug. 22, 2008, now Pat. No. 9,175,015.

(60) Provisional application No. 60/957,208, filed on Aug. 22, 2007.

(51) Int. Cl.

| A61K 9/16 | (2006.01) |
|---|---|
| C08F 8/42 | (2006.01) |
| A61K 49/18 | (2006.01) |
| B82Y 5/00 | (2011.01) |
| C07F 5/00 | (2006.01) |
| A61K 49/00 | (2006.01) |
| A61K 49/12 | (2006.01) |
| C08F 122/36 | (2006.01) |
| A61K 47/48 | (2006.01) |
| A61B 5/055 | (2006.01) |

(52) U.S. Cl.
CPC ............ *C08F 8/42* (2013.01); *A61K 47/48176* (2013.01); *A61K 49/00* (2013.01); *A61K 49/0054* (2013.01); *A61K 49/12* (2013.01); *A61K 49/1818* (2013.01); *A61K 49/1854* (2013.01); *B82Y 5/00* (2013.01); *C07F 5/003* (2013.01); *C08F 122/36* (2013.01); *A61B 5/055* (2013.01); *C07B 2200/11* (2013.01)

(58) Field of Classification Search
None
See application file for complete search history.

(56) References Cited

U.S. PATENT DOCUMENTS

| 4,708,930 A | 11/1987 | Kortright et al. |
|---|---|---|
| 4,743,543 A | 5/1988 | Kortright |

(Continued)

FOREIGN PATENT DOCUMENTS

| WO | 93/11161 A1 | 6/1993 |
|---|---|---|
| WO | 94/13804 A1 | 6/1994 |

(Continued)

OTHER PUBLICATIONS

Amendment and Response to Final Office Action dated Apr. 29, 2015 for U.S. Appl. No. 12/197,044, 8 pages.

(Continued)

*Primary Examiner* — Paul Dickinson
(74) *Attorney, Agent, or Firm* — Dorsey & Whitney LLP

(57) ABSTRACT

The disclosure generally relates to formation of polymers grafted to or polymerized from the surface of gold nanoparticles. The polymers are functionalized to include therapeutic agents and/or targeting agents at their surface, thereby allowing both therapeutic and targeting compounds to be directed to specific cells in a patient.

19 Claims, 9 Drawing Sheets

(56) References Cited

U.S. PATENT DOCUMENTS

| | | | |
|---|---|---|---|
| 4,892,935 | A | 1/1990 | Yoshida et al. |
| 4,914,021 | A | 4/1990 | Toth et al. |
| 4,918,164 | A | 4/1990 | Hellstrom et al. |
| 4,921,789 | A | 5/1990 | Salem et al. |
| 4,939,240 | A | 7/1990 | Chu et al. |
| 4,963,484 | A | 10/1990 | Kufe |
| 5,053,489 | A | 10/1991 | Kufe |
| 5,110,911 | A | 5/1992 | Samuel et al. |
| 5,270,163 | A | 12/1993 | Gold et al. |
| 5,475,096 | A | 12/1995 | Gold et al. |
| 5,512,443 | A | 4/1996 | Schlom et al. |
| 5,545,530 | A | 8/1996 | Satomura et al. |
| 5,693,763 | A | 12/1997 | Codington et al. |
| 5,808,005 | A | 9/1998 | Codington et al. |
| 5,855,866 | A | 1/1999 | Thorpe et al. |
| 5,892,019 | A | 4/1999 | Schlom et al. |
| 5,892,020 | A | 4/1999 | Mezes et al. |
| 7,102,024 | B1 | 9/2006 | Schwartz et al. |
| 7,402,690 | B2 | 7/2008 | McCormick et al. |
| 2002/0165179 | A1 | 11/2002 | Baker, Jr. |
| 2003/0199653 | A1 | 10/2003 | McCormick, III et al. |
| 2004/0052729 | A1 | 3/2004 | Penades et al. |
| 2005/0031692 | A1 | 2/2005 | Beyerinck et al. |
| 2006/0233712 | A1 | 10/2006 | Penades et al. |
| 2007/0123670 | A1 | 5/2007 | McCormick et al. |
| 2009/0060839 | A1 | 3/2009 | Boyes et al. |
| 2009/0060840 | A1 | 3/2009 | Boyes et al. |
| 2012/0052006 | A1 | 3/2012 | Boyes et al. |

FOREIGN PATENT DOCUMENTS

| | | |
|---|---|---|
| WO | 97/38134 A1 | 10/1997 |
| WO | 98/33941 A1 | 8/1998 |
| WO | 99/07724 A1 | 2/1999 |

OTHER PUBLICATIONS

Final Office Action dated Jan. 29, 2015 for U.S. Appl. No. 12/197,044, 8 pages.

US Amendment and Response to Non-Final Office Action dated Jun. 20, 2014 for U.S. Appl. No. 12/197,061 13 pages.

US Response to Final Office Action dated Sep. 19, 2014, U.S. Appl. No. 13/202,311 13 pages.

Amendment and Response to Non-Final Office Action dated Jan. 9, 2015 for for U.S. Appl. No. 12/197,044 12 pages.

International Search Report and Written Opinion, PCT/US2010/024450, dated Jul. 24, 2010; 8 pages.

Adlish et al., "Identification of a Putative Cell Receptor for Human Cytomegalovirus", Virology (1990), 176, 337-345.

Ahrens et al., "A model for MRI contrast enhancement using T1 agents", Proc. Nat'l. Acad. Sci. U.S.A. (1998), 95, 8443-8448.

Aime et al., "A R2R1 Ratiometric Procedure for a Concentration-Independent pH-Responsive, Gd(III)-Based MRI Agent", J. Am. Chem. Soc. (2006), 128, 11326-11327.

Allen "Ligand-Targeted Therapeutics in Anticancer Therapy", Nat. Rev. Cancer (2002), 2, 750-763 and 2 pages.

Alric, Christophe et al., "Gadoliniuim Chelate Coated Gold Nanoparticles as Contrast Agents for Both X-ray Computed Tomography and Magnetic Resonance Imating", J. Am. Chem. Soc., 130, 2008, 5908-5915.

Bakalova et al., "Multimodal Silica-Shelled Quantum Dots: Direct Intracellular Delivery, Photosensitization, Toxic, and Microcirculation Effects", Bioconjugate Chem. (2008), 19, 1135-1142.

Binkley et al., "RNA ligands to human nerve growth factor", Nuc. Acids Res. (1995), 23(16), 3198-3205.

Bird et al., "Single-Chain Antigen-Binding Proteins", Science (1988), 242, 423-426.

Bridot et al., "Hybrid Gadolinium Oxide Nanoparticles: Multimodal Contrast Agents for in Vivo Imaging", J. Am. Chem. Soc. (2007), 129, 5076-5084.

Burda et al., "Chemistry and Properties of Nanocrystals of Different Shapes", Chem. Rev. (2005), 105, 1025-1102.

Caravan et al., "Gadolinium(III) Chelates as MRI Contrast Agents: Structure, Dynammics and Application", Chem. Rev. (1999), 99, 2293-2352.

Carel et al., "Structural Requirements for C3d,g/Epstein-Barr Virus Receptor (CR2/CD21) Ligand Binding, Internalization, and Viral Infection", J. Biol. Chem. (1990), 265(21), 12293-12299.

Carter, "Potent antibody therapeutics by design", Nature Reviews Immunology (2006), 6, 343-357.

Chang, In Pin et al., "Preparation of Fluorescent Magnetic Nanodiamonds and Cellular Imaging", J. Am. Chem. Soc., 2008, 130 (46), 1022/2008, 15476-15481.

Cheon et al., "Synergistically Integrated Nanoparticles as Multimodal Probes for Nanobiotechnology", Accounts of Chem. Res., published online at www.pubs.acs.org/acr (Aug. 13, 2008), 1630-1640.

Co et al., "Isolation and biochemical characterization of the mammalian reovirus type 3 cell-surface receptor", Proc. Nat'l. Acad. Sci. U.S.A (1985), 82, 1494-1498.

Dalgleish, et al., "The CD4 (T4) antigen is an essential component of the receptor for the AIDS retrovirus", Nature (1984), 312, 763-766.

Daniel et al., "Gold Nanoparticles: Assembly, Supramolecular Chemistry, Quantum-Size-Related Properties, and Applications toward Biology, Catalysis, and Nanotechnology", Chem. Rev. (2004), 104(1), 293-346.

Eppstein et al., "Epidermal growth factor receptor occupancy inhibits vaccinia virus infection", Nature (1985), 318, 663-665.

Ferrari, "Cancer Nanotechnology: Opportunities and Challenges", Nature Rev. Cancer (2005), 5, 161-171.

Frullano et al., "Multimodal MRI Contrast Agents", J. Biol. Inorg. Chem. (2007), 12, 939-949.

Fu et al., "Cascade Polymeric MRI Contrast Media Derived from Poly(ethylene glycol) Cores: Initial Syntheses and Characterizations", Biomacromolecules (2007), 8, 1519-1529.

Fustin et al., "Tuning the hydrophilicity of gold nanoparticles templated in star block copolymers", Langmuir (2006), 22, 6690-6695.

Hanisch et al., "Structural Studies on Oncofetal Carbohydrate Antigens (CA 19-9, CA 50, and CA 125) Carried by O-Linked Sialyloligosaccharides on Human Amniotic Mucins", Carbohydr. Res. (1988), 178, 29-47.

Harlow et al., "Using Antibodies: A Laboratory Manual", Cold Spring Harbor, New York, Cold Spring Harbor Laboratory Press, 1999, 5 pages.

Hifumi et al., "Gadolinium-Based Hybrid Nanoparticles as a Positive MR Contrast Agent", J. Am. Chem. Soc. (2006), 128(47), 15090-15091.

High et al., "Gadolinium is detectable within the tissue of patients with nephrogenic systemic fibrosis", J. Am. Acad. Dermatol. (2007), 56, 21-26.

Hinoda et al., "Immunochemical Characterization of Adenocarcinoma-Associated Antigen YH206", Int'l Cancer Journal (1988), 42, 653-658.

Holliger et al., "Diabodies: Small bivalent and bispecific antibody fragments", Proc. Natl. Acad. Sci. USA (1993) 90, 6444-6448.

Holliger, et al., "Engineered antibody fragments and the rise of single domains: Antibody engineering and manufacture", Nature Biotech (2005), 23(9), 1126-1136.

Huang et al., "Cancer Cell Imaging and Photothermal Therapy in the Near-Infrared Region by Using Gold Nanorods", J. Am. Chem. Soc. (2006), 128, 2115-2120.

Huston et al., "Protein engineering of antibody binding sites: Recovery of specific activity in an anti-digoxin single-chain Fv analogue produced in *Escherichia coli*", Proc. Natl. Acad. Sci. U.S.A. (1988), 85, 5879-5883.

Ishida et al., "Related Glycoprotiens from Normal Secretory and Malignant Brest Cells: Purification and Intitial Comparative Characterizations", Tumor Biol. (1989), 10, 12-22 and 1 page.

Jellinek et al., "Inhibition of Receptor Binding by High-Affinity RNA Ligands to Vascular Endothelial Growth Factor", Biochem. (1994), 33(34) 10450-10456.

(56) References Cited

OTHER PUBLICATIONS

Kaner et al., "Fibroblast Growth Factor Receptor is a Portal of Cellular Entry for Herpes Simplex Virus Type 1", Science (1990), 248, 1410-1413.
Kim et al., "Antibiofouling Polymer-Coated Gold Nanoparticles as a Contrast Agent for in Vivo X-ray Computed Tomography Imaging", J. Am. Chem. Soc. (2007), 129, 7661-7665.
Kjeldsen, "Preparation and Characterization of Monoclonal Antibodies Directed to the Tumor-associated O-linked Sailosyl-2-6 a-N-Acetylgalactosaminyl (Sialosyl-Tn) Epitope", Cancer Research (1988), 48, 2214-2220.
Klatzmann et al., "T-lymphocyte T4 molecule behaves as the receptor for human retrovirus LAV", Nature (1984), 312, 767-768.
Konopacki et al., "Polymer Modified Gold and Gadolinium Nanoparticles for Targeted Imaging and Treatment of Cancer", Department of Chemistry and Geochemstry Colorado School of Mines, Golden, Colorado, 2 pages.
Krah et al., "Characterization of Octyl Glucoside-Solubilized Cell Membrane Receptors for Binding Measles Virus", Virology (1989), 172, 386-390.
Kukowska-Latallo et al., "Nanoparticle Targeting of Anticancer Drug Improves Therapeutic Response in Animal Model of Human Epithelial Cancer", Cancer Research (2005), 65, 5317-5324.
Lan et al., "Isolation and Properties of a Human Pancreatic Adenocarcinoma-associated Antigen, DU-PAN-2", Cancer Res. (1985), 45, 305-310.
Lentz et al., "Is the Acetylcholine Receptor a Rabies Virus Receptor?", Science (1982), 215, 182-184.
Lowe, et al., "Facile preparation of transition metal nanoparticles stabilized by well-defined (Co)polymers synthesized via aqueous reversible addition-fragmentation chain transfer polymerization", J. Am. Chem. Soc. (2002), 124, 11562-11563.
Lu et al., "Mesoporous Silica Nanoparticles as a Delivery System for Hydrophobic Anticancer Drugs", Small (2007), 3(8), 1341-1346.
Marlin et al., "A soluble form of intercellular adhesion molecule-1 inhibits rhinovirus infection", Nature (1990), 344, 70-72.
Martin et al., "Nanomaterials in Analytical Chemistry", Analytical Chem. News & Features, May 1, 1998, 322-327, 12 pages.
Mendelsohn, "Cellular Receptor for Poliovirus: Molecular Cloning, Nucleotide Sequence, and Expression of a New Member of the Immunoglobulin Superfamily", Cell (1989), 56, 855-865.
Murphy et al., "Anisotropic Metal Nanoparticles: Synthesis, Assembly, and Optical Applications", J. Phys. Chem. B (2005), 109, 13857-13870.
Nasongkla et al., "Multifunctional Polymeric Micelles as Cancer-Targeted, MRI-Ultrasensitive Drug Delivery Systems", Nano Letters (2006), 6(11), 2427-2430.
Niidome et al., "PEG-modified gold nanorods with a stealth character for in vivo applications", J. Controlled Release (2006), 114, 343-347.
Odian, "Principles of Polymerization", 4th Edition, Hoboken, New Jersey, Wiley-Interscience, 2004, 19 pages.
Oyewumi, "Comparison of cell uptake, biodistribution and tumor retention of folate-coated and PEG-coated gadolinium nanoparticles in tumor-bearing mice", Journal of Controlled Release (2004), 95, 613-626.
Park, "Nanotechnology: What it can do for drug delivery", J. Controlled Release (2007), 120, 1-3.
Park, "Tumor-directed Targeting of Liposomes", Biosci. Rep. (2002), 22(2), 267-281.
Perez-Juste et al., "Gold-nanorods: Synthesis, characterization and applications", Coordination Chemistry Reviews (2005), 249, 1870-1901.
Non-Final Office Action dated Sep. 9, 2014 for U.S. Appl. No. 12/197,044, 13 pages.
PCT International Search Report dated Dec. 19, 2008, PCT Application No. PCT/US2008/74065, filed Aug. 22, 2008, 3 pages.
US Amendment and Response to Non-Final Office Action dated Nov. 21, 2011, U.S. Appl. No. 12/197,044, 11 pages.
US Amendment/Request Reconsideration—After Non-Final Rejection dated Jan. 9, 2012, U.S. Appl. No. 12/197,061, 22 pages.
US Final Rejection Office Action dated Apr. 25, 2012, U.S. Appl. No. 12/197,061, 13 pages.
US Non-Final Rejection Office Action dated Mar. 20, 2014, U.S. Appl. No. 12/197,061, 15 pages.
US Non-Final Rejection Office action dated Oct. 7, 2011, U.S. Appl. No. 12/197,061, 12 pages.
US Notice of Appeal dated Aug. 27, 2012, U.S. Appl. No. 12/197,061, 1 page.
US Notice of Appeal dated May 3, 2012, U.S. Appl. No. 12/197,044, 1 page.
US Notice of Final Rejection dated Jan. 4, 2012, U.S. Appl. No. 12/197,044, 6 pages.
US Notice of Non-Final Rejection dated May 19, 2011, U.S. Appl. No. 12/197,044, 7 pages.
US Pre-Appeal Brief Request for Review and Arguments dated May 3, 2012, U.S. Appl. No. 12/197,044, 5 pages.
US Pre-Brief Appeal Conference Decision dated Oct. 17, 2012, U.S. Appl. No. 12/197,061, 2 pages.
US Pre-Brief Conference Request dated Aug. 27, 2012, U.S. Appl. No. 12/9701,661, 5 pages.
US Request for Continued Examination dated May 3, 2012, U.S. Appl. No. 12/197,044, 3 pages.
US Requirement for Restriction/Election dated Jun. 3, 2011, U.S. Appl. No. 12/197,061, 6 pages.
US Response to Election/Restriction dated Jul. 5, 2011, U.S. Appl. No. 12/197,061, 6 pages.
US Response to Election/Restriction dated Mar. 4, 2011, U.S. Appl. No. 12/197,044, 7 pages.
US Restriction/Election Requirement dated Feb. 4, 2011, U.S. Appl. No. 12/197,044, 8 pages.
US Non-Final Rejection dated Dec. 4, 2013, U.S. Appl. No. 13/202,311, 18 pages.
US Notice regarding Non-Compliant or Non-Responsive Amendment dated Jul. 5, 2013, U.S. Appl. No. 13/202,311, 2 pages.
US Response to Election / Restriction dated Nov. 19, 2012, U.S. Appl. No. 13/202,311, 12 pages.
US Response to Non-Final Office Action dated Jun. 4, 2014, U.S. Appl. No. 13/202,311, 15 pages.
US Restriction/Election Requirement dated Sep. 20, 2012, U.S. Appl. No. 13/202,311, 12 pages.
US Supplemental Response or Amendment to Notice regarding Non-Compliant or Non-Responsive Amendment dated Jul. 26, 2013, U.S. Appl. No. 13/202,311, 9 pages.
US Final Office Action dated Jun. 20, 2014, U.S. Appl. No. 13/202,311, 20 pages.
US Request for Continued Examination dated Dec. 14, 2012, U.S. Appl. No. 12/197,061, 19 pages.
Remington, "Practice of the Science and Pharmacy", 19th Edition, Alfonso R. Gennaro, ed., (1995) Chapter 83, 1447-1675 and 3 cover pages.
Rieter et al., "Nanoscale Metal-Organic Frameworks as Potential Multimodal Contrast Enhancing Agents", J. Am Chem. Soc. (2006), 128, 9024-9025.
Rieter et al., "Surface Modification and Functionalization of Nanoscale Metal-Organic Frameworks for Controlled Release and Luminescence Sensing", J. Am. Chem. Soc., May 17, 2007, 2 pages.
Rowe et al., "Synthesis of Surface-Initiated Stimuli-Responsive Diblock Copolymer Brushes Utilizing a Combination of ATRP and RAFT Polymerization Techniques", Macromolecules (2008), 41(12), 4147-4157.
Rowe-Konopacki et al., "Synthesis of Surface Initiated Diblock Copolymer Brushes from Flat Silicon Substrates Utilizing the RAFT Polymerization Technique", Macromolecules (2007), 40(4), 879-888.
Ruff et al., "CD4 receptor binding peptides that block HIV infectivity cause human monocyte chemotaxis", FEBS Letters (1987), 211(1), 17-22.
Sacerdote et al., "Vasoactive Intestinal Peptide 1-12: A Ligand for the CD4 (T4)/Human Immunodeficiency Virus Receptor", J. Neuroscience Research (1987), 18, 102-107 and 1 page.
Sau et al., "Seeded High Yield Synthesis of Short Au Nanorods in Aqueous Solution", Langmuir (2004), 20(15), 6414-6420.

(56) References Cited

OTHER PUBLICATIONS

Sebra, "Surface Grafted Antibodies: Controlled Architecture Permits Enhanced Antigen Detection", Langmuir (2005), 21(24), 10907-10911.
Seevinck et al., "Factors Affecting the Sensitivity and Detection Limits of MRI, CT, and SPECT for Multimodal Diagnostic and Therapeutic Agents", Anti-Cancer Agent in Medicinal Chemistry (Formerly Current Medicinal Chemistry—Anti-Cancer Agents), vol. 7, No. 3, May 2007, 317-334(18).
Service, "Nanotechnology Takes Aim at Cancer", Science (2005), 310, 1132-1134.
Shepley et al., "Monoclonal antibody identification of a 100-kDa membrane protein in HeLa cells and human spinal cord involved in poliovirus attachment", Proc. Nat'l. Acad. Sci. U.S.A. (1988), 85, 7743-7747.
Slavin, Stacy et al., "Adsorption behaviour of sulfur containing polymers to gold surfaces using QCM-D", Soft Matter, 2012, 8, 118-128, DOI: 10.1039/clsm06410j.
Slowing et al., "Mesoporous Silica Nanoparticles for Intracellular Delivery of Membrane-Impermeable Proteins", J. Am. Chem. Soc. (2007), 129, 8845-8849.
Solberg et al., "Adsorption of DNA into Mesoporous Silica", J. Phys. Chem. B. (2006), 110(31), 15261-15268.
Springer et al., "Blood Group Tn-Active Macromolecules from Human Carcinomas and Erythrocytes: Characterization of and Specific Reactivity with Mono- and Poly-Clonal Anti-Tn Antibodies Induced by Various Immunogens", Carbohydr. Res. (1988), 178, 271-292.
Stenzel, Martina H. , "Hairy Core-Shell Nanoparticles via RAFT: Where are the Opportunities and Where are the Problems and Challenges?", Macromol. Rapid Commun. 2009, 30, 1603-1624, DOI: 10.1002/marc.200900180.
Su, et al., "Nanoshell Magnetic Resonance Imaging Contrast Agents", J. Am. Chem. Soc. (2007), 129, 2139-2146.
Sumerlin et al., "Modification of gold surfaces with water-soluble (Co)polymers prepared via aqueous reversible addition-fragmentation chain transfer (RAFT) polymerization", Langmuir (2003), 19, 5559-5562.
Tjandra et al., "Application of mammary serum antigen assay in the management of breast cancer: a preliminary report", Br. J. Surg. (1988), 75(8), 811-817.
Tomlinson et al., "Methods for Generating Multivalent and Bispecific Antibody Fragments", Methods in Enzymology (2000), 326, 461-479.
Tuerk et al., "In vitro evolution of functional nucleic acids: high-affinity RNA ligands of HIV-1 proteins", Gene. (1993), 137, 33-39.
Ward et al., "Binding activities of a repertoire of single immunoglobulin variable domains secreted from *Escherichia coli*", Nature (Oct. 12, 1989), 341, 544-546.
Weis et al., "Structure of the influenza virus haemagglutinin complexed with its receptor, sialic acid", Nature (1988), 333, 426-431.
White et al., "Viral Receptors of the Immunoglobulin Superfamily", Cell (1989), 56, 725-728.
Wyrick et al., "Entry of Genital Chlamydia trachomatis into Polarized Human Epithelial Cells", Infect. and Immunity (1989), 57(8), 2378-2389.
Yanjarappa, "Synthesis of Copolymers Containing an Active Ester of Methacrylic Acid by RAFT: Controlled Molecular Weight Scaffolds for Biofunctionalization", Biomacromolecules (2006), 7(5), 1665-1670.
Zola (Ed.), "Monoclonal Antibodies: Preparation and use of monoclonal antibodies and engineered antibody derivatives," 2000, Springer Verlag, 1st Edition, 1st Edition, New York, New York, Springer Verlag, 2000, 5 pages.

GOLD NANOPARTICLE CONJUGATES AND USES THEREOF

CROSS REFERENCE TO RELATED APPLICATIONS

This application is a divisional application of U.S. patent application Ser. No. 12/197,044, entitled "Gold Nanoparticle Conjugates and Uses Thereof," filed Aug. 22, 2008, which claims the benefit of priority under 35 U.S.C. §119(e) of U.S. Provisional Application No. 60/957,208 entitled "Gadolinium and Gold Nanoparticle Conjugates and Uses Thereof," filed Aug. 22, 2007, each of which is hereby incorporated by reference in its entirety. This application is also related to U.S. patent application Ser. No. 12/197,061 entitled "Lanthanide Nanoparticle Conjugates and Uses Thereof," filed Aug. 22, 2008, which has issued as U.S. Pat. No. 8,916,135, and to co-pending U.S. patent application Ser. No. 14/580,827, entitled "Lanthanide Nanoparticle Conjugates and Uses Thereof," filed Dec. 23, 2014, each of which is hereby incorporated by reference in its entirety.

FIELD

The disclosure generally relates to formation of polymers grafted to or polymerized from the surface of gold nanoparticles. The polymers are functionalized to include therapeutic agents and targeting agents at their surface, thereby allowing both imaging and targeting therapeutic compounds to specific cells in a patient.

BACKGROUND

One of the most important areas of research in the general field of nanotechnology is in the development of nanomedicines, which refers to highly specific medical intervention at the molecular scale for diagnosis, prevention, and treatment of diseases. See, e.g. Park, K. *J. Controlled Release* 2007, 120, 1-3. The importance of this area is highlighted by the recent establishment of the National Institutes of Health (NIH) Nanomedicine Roadmap Initiative (http://nihroadmap.nih.gov/nanomedicine/), where over $1 billion has been committed in an attempt to revolutionize the areas of therapeutics and diagnostics through the development and application of nanotechnology and nanodevices. One of the most exciting areas of nanomedicine is the development of nanodevices for theragnostics, which refers to a combination of diagnostics and therapeutics for tailored treatment of diseases. The synthesis of nanodevices that incorporate therapeutic agents, molecular targeting, and diagnostic imaging capabilities have been described as the next generation nanomedicines and have the potential to dramatically improve the therapeutic outcome of drug therapy (e.g. Nasongkla, N. et al. *Nano Lett.* 2006, 6, 2427-2430) and lead to the development of personalized medicine, where the device may be tailored for treatment of individual patients on the basis of their genetic profiles. While there is almost unanimous agreement in the scientific community that these next generation nanomedicines will provide clinically important theragnosis devices, they have yet to be clinically realized.

One of the primary reasons for this is the poor design and manufacturing techniques of the current nanodevices. The main problems with the current manufacturing techniques include low drug and/or targeting moiety loading capacity, low loading efficiencies, and poor ability to control the size distribution, surface interactions, and in vivo performance of the devices. See, e.g., Park, K. J. *Controlled Release* 2007, 120, 1-3. In conjunction to these manufacturing problems, current design issues center around a lack of flexibility in the construct which may limit the type and quantity of drug and/or targeting agent that may be incorporated, provide little or no control over spatial orientation and architecture of the nanoparticle, and have stability issues with the particle structure or with the drug and/or targeting agent incorporated in the particle.

Recently polymer-based nanodevices have received much attention and many believe that they are the most promising for clinical translation. See, e.g., Bridot, J.-L., et al. *J. Am. Chem. Soc.* 2007. Examples of polymer-based theragnostic nanodevices includes dendrimers, polymeric micelles, and polymer-based core-shell nanoparticles. While dendrimers have proven to be effective for drug delivery or targeted molecular imaging, it is difficult to control the loading capacity and efficiency of the drug, imaging and/or targeting agent. Polymeric micelles use a hydrophobic core to carry therapeutics and imaging agents, while targeting agents are attached to the hydrophilic corona. However, micelle structures are susceptible to instabilities due to changes in the surrounding in vivo environment and have limited control of loading capacity. Polymer-based core-shell nanoparticles offer improved stability over polymer micelles; however, it is often difficult to release therapeutic agents contained within the core of the structure which tends to inhibit their therapeutic value.

One area that has reached significant commercial application is the use of targeted drug delivery. This represents an extremely diverse area due to the large number of diseases that potentially benefit from targeted delivery. As the current focus of research into the invention has been on the targeted imaging and treatment of cancer, this discussion will focus on competitive products in the areas of cancer therapy and diagnosis. However, the flexibility of the invention allows for its potential use in any disease that would benefit from theragnosis.

The present disclosure has been developed against this backdrop.

SUMMARY

The present disclosure is directed generally to gold nanoparticle conjugates, particularly to polymers, and the subsequent conjugation to targeting agents and therapeutic agents, and their use in targeting, treating, and/or imaging disease states in a patient. In certain embodiments, the gold nanoparticle conjugates are multifunctional polymeric systems. Biocompatible polymer backbones that can be conjugated to imaging agents, targeting agents, and therapeutic agents are produced. Post-polymerization modification of the polymer backbone allows attachment of targeting agents or therapeutic agents to a functional group. The resulting gold nanoparticle conjugates provide the ability to target, treat, and image diseased cells.

In one aspect, gold nanoparticle conjugates are provided. The conjugate includes a gold nanoparticle and a polymer or polymer precursor containing a functional group attached to the nanoparticle. As used herein, polymer precursors include components of polymers, such as monomers, dimers, etc., or initiators bonded to the gold nanoparticle prior to polymerization. In various aspects, the functional group is selected from the group consisting of thiolates, thioethers, thioesters, carboxylates, amines, amides, halides, phosphonates, phosphonate esters, phosphinates, sulphonates, sulphates, porphyrins, nitrates, pyridine, pyridyl based compounds, nitrogen containing ligands, oxygen containing ligands, and sulfur containing ligands. In certain embodiments, the polymer, polymer precursor or initiator can be grafted onto the gold nanoparticle by a covalent or non-covalent bond between a functional group and nanoparticle. In certain embodiments, the functional group is a single thiol group and vacant orbital present on the gold (III) cation. In further aspects, the gold nanoparticle conjugate can have the chemical structure according to formulae (I) or (II):

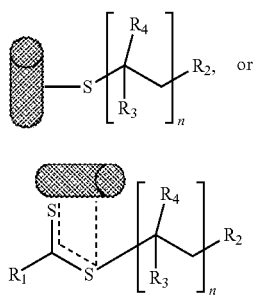

wherein n is an integer, $R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

In other embodiments, $R_2$ includes a functional group selected from thiolates, thioethers, thioesters, carboxylates, amines, amides, halides, phosphonates, phosphonate esters, phosphinates, sulphonates, sulphates, porphyrins, nitrates, pyridine, pyridyl based compounds, nitrogen containing ligands, oxygen containing ligands, and sulfur containing ligands.

The polymer portion of the nanoparticle conjugate can include a dithioester, trithiocarbonate, xanthate, or dithiocarbamate chain termination agent, and/or a functional group such as carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives. The gold nanoparticle conjugate can further include a therapeutic agent and/or a targeting agent, each covalently bonded to said polymer.

In another aspect, the disclosure is directed to a pharmaceutical composition comprising the gold nanoparticle conjugate as described herein, and a pharmaceutically acceptable carrier.

In a further aspect, the disclosure is directed to a method of making gold nanoparticle conjugates. A gold nanoparticle having a suitable initiator is contacted with a dithioester, xanthate, or dithiocarbamate of formulae (III) or a trithiocarbonate of formulae (IV):

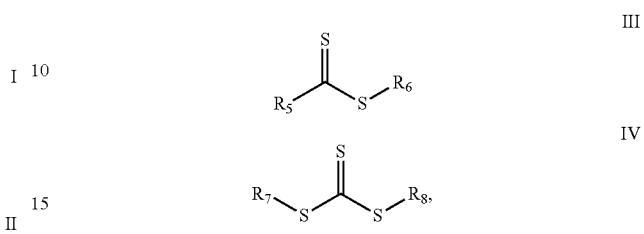

wherein $R_5$, $R_6$, $R_7$, and $R_8$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

In other embodiments, $R_6$ and $R_8$ are each independently selected from a dithioester, xanthate, dithiocarbamate and trithiocarbonate. The compounds of formulae (III) and (IV) are contacted with a reducing agent. The reduced compounds are then contacted with a gold nanoparticle to form a gold nanoparticle conjugate.

In further aspects, the disclosure is directed to a method of treating a disease or disorder by administering a gold nanoparticle conjugate to a patient in need of treatment of said disease or disorder. In various embodiments, the targeting agent localizes the nanoparticle conjugate to the site of the disease or disorder. The therapeutic agent treats said disease or disorder. The method can be further combined with imaging the gold nanoparticle conjugate at the disease location.

BRIEF DESCRIPTION OF THE DRAWINGS

The disclosed Figures are exemplary, and are not intended to be limiting of the claims.

DETAILED DESCRIPTION

Figure 1:
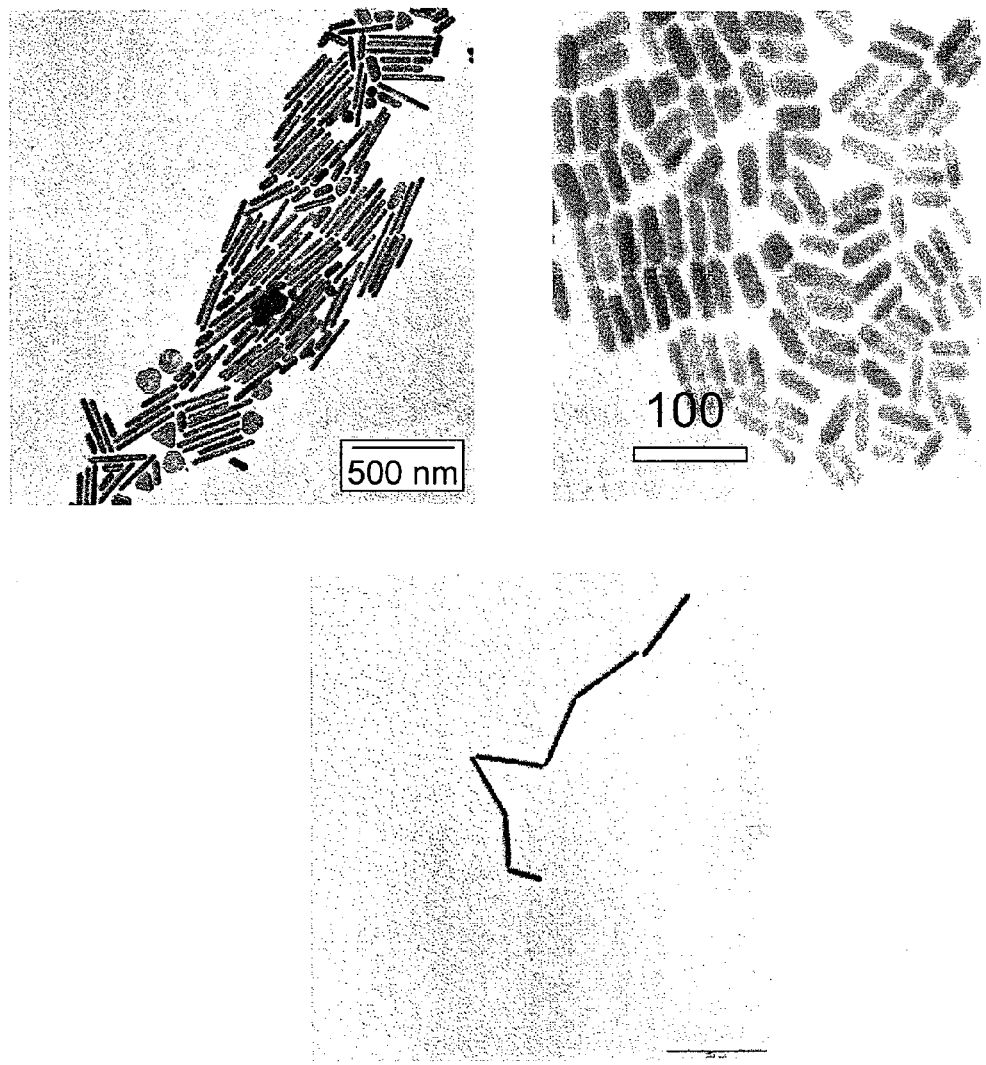
FIG. 1 depicts transmission electron microscope (TEM) images of various exemplary gold nanorod structures.

There has been an increasing focus on the development of multifunctional nanomedicines for improvement in the remedial results of drug treatment for cancer patients. See, e.g., Kukowska-Latallo, J. F. et al., *Langmuir* 2004, 20, 6414-6420, Niidome, T. et al. *Journal of Controlled Release* 2006, 114, 343-347. Multifunctional nanomedicines incorporate diagnostic imaging capabilities, targeting through biomolecular recognition, and a therapeutic agent for treatment of a specific disease, providing a "one dose" approach of overcoming downfalls of conventional treatment and imaging techniques.

The present disclosure relates to preparation of gold nanoparticle conjugates comprising a gold nanoparticle grafted onto a polymer or polymer precursor comprising a functional group. The functional group serves as the point of attachment to the gold nanoparticle. Thus, molecules are specifically bonded to gold nanoparticles by a specific functional group. The nanoparticle conjugates are then further functionalized to include a therapeutic and/or diagnostic agent.

Definitions

A dash ("-") that is not between two letters or symbols is used to indicate a point of attachment for a moiety or substituent. For example, —CONH$_2$ is attached through the carbon atom.

"Grafting" or "grafted onto" as used herein refers to attaching a polymer, polymer precursor or small molecule to the surface of a nanoparticle via a single functional group. Grafting includes both covalent and non-covalent binding, as well as, but not limited to, delocalized bond formation between one or more atoms of the nanoparticle and one or more atoms of the functional group, ionic bonding, hydrogen bonding, dipole-dipole bonding, and van der Waals forces. Formation of exemplary bonds are depicted in Schemes 2 and 3 described herein. The terms "grafting" and "grafting onto" include methods conventionally referred to as grafting from and grafting to.

"Covalent grafting" as used herein refers to attaching a polymer, polymer precursor, or small molecule by one or more covalent bonds from a functional group to the surface of a nanoparticle or by a delocalized bond complex, such as a delocalized bond complex.

"Alkyl" by itself or as part of another substituent refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl(allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In certain embodiments, an alkyl group can have from 1 to 20 carbon atoms ($C_{1-20}$) in certain embodiments, from 1 to 10 carbon atoms ($C_{1-10}$), in certain embodiments from 1 to 8 carbon atoms ($C_{1-8}$), in certain embodiments, from 1 to 6 carbon atoms ($C_{1-6}$), in certain embodiments, from 1 to 4 carbon atoms ($C_{1-4}$), and in certain embodiments, from 1 to 3 carbon atoms ($C_{1-3}$).

"Alkanyl" by itself or as part of another substituent refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl(t-butyl), cyclobutan-1-yl, etc.; and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl(allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl or heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" by itself or as part of another substituent refers to a radical —NR$^{31}$C(O)R$^{32}$, where R$^{31}$ and R$^{32}$ are independently hydrogen, alkyl, cycloalkyl, cycloheteroalkyl, aryl, arylalkyl, heteroalkyl, heteroaryl or heteroarylalkyl as defined herein. Representative examples include, but are not limited to formamido, acetamido and benzamido.

"Acyloxy" by itself or as part of another substituent refers to a radical —OC(O)R$^{33}$, where R$^{33}$ is alkyl, cycloalkyl, cycloheteroalkyl, aryl, arylalkyl, heteroalkyl, heteroaryl or heteroarylalkyl as defined herein. Representative examples include, but are not limited to acetoxy, isobutyroyloxy, benzoyloxy, phenylacetoxy and the like.

"Alkoxy" by itself or as part of another substituent refers to a radical —OR$^{34}$ where R$^{34}$ represents an alkyl or cycloalkyl group as defined herein. Representative examples include, but are not limited to, methoxy, ethoxy, propoxy, butoxy, cyclohexyloxy and the like.

"Alkylamino" means a radical —NHR where R represents an alkyl or cycloalkyl group as defined herein. Representative examples include, but are not limited to, methylamino, ethylamino, 1-methylethylamino, cyclohexyl amino and the like.

"Alkoxycarbonyl" by itself or as part of another substituent refers to a radical —C(O)—OR$^{35}$ where R$^{35}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Alkoxycarbonylamino" by itself or as part of another substituent refers to a radical —NR$^{36}$C(O)—OR$^{37}$ where R$^{36}$ represents an alkyl or cycloalkyl group and R$^{37}$ is alkyl, cycloalkyl, cycloheteroalkyl, aryl, arylalkyl, heteroalkyl, heteroaryl, heteroarylalkyl as defined herein. Representative examples include, but are not limited to, methoxycarbonylamino, tert-butoxycarbonylamino and benzyloxycarbonylamino.

"Alkoxycarbonyloxy" by itself or as part of another substituent refers to a radical —OC(O)—OR$^{38}$ where R$^{38}$ represents an alkyl or cycloalkyl group as defined herein. Representative examples include, but are not limited to, methoxycarbonyloxy, ethoxycarbonyloxy and cyclohexyloxycarbonyloxy.

"Alkylsulfinyl" refers to a radical —S(O)R where R is an alkyl or cycloalkyl group as defined herein. Representative examples include, but are not limited to, methylsulfinyl, ethylsulfinyl, propylsulfinyl, butylsulfinyl and the like.

"Alkylsulfonyl" refers to a radical —S(O)$_2$R where R is an alkyl or cycloalkyl group as defined herein. Representative examples include, but are not limited to, methylsulfonyl, ethylsulfonyl, propylsulfonyl, butylsulfonyl and the like.

"Alkylthio" refers to a radical —SR where R is an alkyl or cycloalkyl group as defined herein that may be optionally substituted as defined herein. Representative examples include, but are not limited to methylthio, ethylthio, propylthio, butylthio and the like.

"Aryl" by itself or as part of another substituent refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group is from 6 to 20 carbon atoms. In other embodiments, an aryl group is from 6 to 12 carbon atoms.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is (C$_6$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). In other embodiments, an arylalkyl group is (C$_6$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Aryloxycarbonyl" refers to a radical —C(O)—O-aryl where aryl is as defined herein.

"Aryloxy" refers to a radical —C—O-aryl where aryl is as defined herein.

"Carbamoyl" by itself or as part of another substituent refers to the radical —C(O)NR$^{39}$R$^{40}$ where R$^{39}$ and R$^{40}$ are independently hydrogen, alkyl, cycloalkyl or aryl as defined herein.

"Carbamoyloxy" by itself or as part of another substituent refers to the radical —OC(O)NR$^{41}$R$^{42}$ where R$^{41}$ and R$^{42}$ are independently hydrogen, alkyl, cycloalkyl or aryl as defined herein.

"Compounds" of as defined by a chemical formula as disclosed herein include any specific compounds within the formula. Compounds may be identified either by their chemical structure and/or chemical name. When the chemical structure and chemical name conflict, the chemical structure is determinative of the identity of the compound. The compounds described herein may comprise one or more chiral centers and/or double bonds and therefore may exist as stereoisomers such as double-bond isomers (i.e., geometric isomers), enantiomers, or diastereomers. Accordingly, any chemical structures within the scope of the specification depicted, in whole or in part, with a relative configuration encompass all possible enantiomers and stereoisomers of the illustrated compounds including the stereoisomerically pure form (e.g., geometrically pure, enantiomerically pure, or diastereomerically pure) and enantiomeric and stereoisomeric mixtures. Enantiomeric and stereoisomeric mixtures may be resolved into their component enantiomers or stereoisomers using separation techniques or chiral synthesis techniques well known to the skilled artisan.

Compounds include, but are not limited to, optical isomers of compounds, racemates thereof, and other mixtures thereof. In such embodiments, the single enantiomers or diastereomers, i.e., optically active forms, can be obtained by asymmetric synthesis or by resolution of the racemates. Resolution of the racemates may be accomplished, for example, by conventional methods such as crystallization in the presence of a resolving agent, or chromatography, using, for example a chiral high-pressure liquid chromatography (HPLC) column. In addition, compounds can include Z- and E-forms (or cis- and trans-forms) of compounds with double bonds.

Compounds may also include isotopically labeled compounds where one or more atoms have an atomic mass different from the atomic mass conventionally found in nature. Examples of isotopes that may be incorporated into the compounds disclosed herein include, but are not limited to, $^2$H, $^3$H, $^{11}$C, $^{13}$C, $^{14}$C, $^{15}$N, $^{18}$O, $^{17}$O, etc. Compounds may exist in unsolvated forms as well as solvated forms, including hydrated forms and as N-oxides. In general, compounds as referred to herein may be free acid, hydrated, solvated, or N-oxides of a Formula. Certain compounds may exist in multiple crystalline, co-crystalline, or amorphous forms. Compounds include pharmaceutically acceptable salts thereof, or pharmaceutically acceptable solvates of the free acid form of any of the foregoing, as well as crystalline forms of any of the foregoing.

"Pharmaceutically acceptable salt" refers to a salt of a compound, which possesses the desired pharmacological activity of the parent compound. Such salts include acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxy-ethanesulfonic acid, benzenesulfonic acid, 4-chlorobenzene-sulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine, and the like. In certain embodiments, a pharmaceutically acceptable salt is the hydrochloride salt. In certain embodiments, a pharmaceutically acceptable salt is the sodium salt.

"Salt" refers to a salt of a compound, including, but not limited to, pharmaceutically acceptable salts.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which a compound provided by the present disclosure may be administered to a patient and which does not destroy the pharmacological activity thereof and which is non-toxic when administered in doses sufficient to provide a therapeutically effective amount of the compound.

"Pharmaceutical composition" refers to a compound of Formula (I) or Formula (II) and at least one pharmaceutically acceptable vehicle, with which the compound of Formula (I) or Formula (II) is administered to a patient.

"Solvate" refers to a molecular complex of a compound with one or more solvent molecules in a stoichiometric or non-stoichiometric amount. Such solvent molecules are those commonly used in the pharmaceutical art, which are known to be innocuous to a patient, e.g., water, ethanol, and the like. A molecular complex of a compound or moiety of a compound and a solvent can be stabilized by non-covalent intramolecular forces such as, for example, electrostatic forces, van der Waals forces, or hydrogen bonds. The term "hydrate" refers to a solvate in which the one or more solvent molecules is water.

"Conjugate acid of an organic base" refers to the protonated form of a primary, secondary or tertiary amine or heteroaromatic nitrogen base. Representative examples include, but are not limited to, triethylammonium, morpholinium and pyridinium.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In some embodiments, the cycloalkyl group is ($C_3$-$C_{10}$)cycloalkyl. In other embodiments, the cycloalkyl group is ($C_3$-$C_7$)cycloalkyl.

"Cycloheteroalkyl" by itself or as part of another substituent refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine, and the like.

"Dialkylamino" by itself or as part of another substituent refers to the radical —NR$^{43}$R$^{44}$ where R$^{43}$ and R$^{44}$ are independently alkyl, cycloalkyl, cycloheteroalkyl, arylalkyl, heteroalkyl or heteroarylalkyl, or optionally R$^{43}$ and R$^{44}$ together with the nitrogen to which they are attached form a cycloheteroalkyl ring.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —O—O—, —S—S—, —O—S—, —NR$^{45}$R$^{46}$, =N—N=, —N=N—, —N=N—NR$^{47}$R$^{48}$, —PR$^{49}$—, —P(O)$_2$—, —POR$^{50}$—, —O—P(O)$_2$—, —SO—, —SO$_2$—, —SnR$^{51}$R$^{52}$— and the like, where R$^{45}$, R$^{46}$, R$^{47}$, R$^{48}$, R$^{49}$, R$^{50}$, R$^{51}$ and R$^{52}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Certain heteroaryl groups are those derived from thiophene, pyrrole, benzothiophene, benzofuran, indole, pyridine, quinoline, imidazole, oxazole and pyrazine "Heteroarylalkyl" by itself or as part of another substituent refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In some embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In other embodiments, the heteroarylalkyl group is a 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Sulfonamido" by itself or as part of another substituent refers to a radical —NR$^{53}$S(O)$_2$R$^{54}$, where R$^{53}$ is alkyl, substituted alkyl, cycloalkyl, cycloheteroalkyl, aryl, substituted aryl, arylalkyl, heteroalkyl, heteroaryl or heteroarylalkyl and R$^{54}$ is hydrogen, alkyl, cycloalkyl, cycloheteroalkyl, aryl, arylalkyl, heteroalkyl, heteroaryl or heteroarylalkyl as defined herein. Representative examples include, but are not limited to methanesulfonamido, benzenesulfonamido and p-toluenesulfonamido.

"Aromatic Ring System" by itself or as part of another substituent refers to an unsaturated cyclic or polycyclic ring system radical having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent refers to a aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Halo" means fluoro, chloro, bromo, or iodo radical.

"Heteroalkyloxy" means an —O-heteroalkyl where heteroalkyl is as defined herein.

"Heteroaryloxycarbonyl" refers to a radical —C(O)—OR where R is heteroaryl as defined herein.

"Substituted" refers to a group in which one or more hydrogen atoms are each independently replaced with the same or different substituent(s). Typical substituents include, but are not limited to, —X, —R$^{29}$, —O$^-$, =O, —OR$^{29}$, —SR$^{29}$, —S$^-$, =S, —NR$^{29}$R$^{30}$, =NR$^{29}$, —CX$_3$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{29}$, —OS(O$_2$)O$^-$, —OS(O)$_2$R$^{29}$, —P(O)(O$^-$)$_2$, —P(O)(OR$^{29}$)(O$^-$), —OP(O)(OR$^{29}$)(OR$^{30}$), —C(O)R$^{29}$, —C(S)R$^{29}$, —C(O)OR$^{29}$, —C(O)NR$^{29}$R$^{30}$, —C(O)O$^-$, —C(S)OR$^{29}$, —NR$^{31}$C(O)NR$^{29}$R$^{30}$, —NR$^{31}$C(S)NR$^{29}$R$^{30}$, —NR$^{31}$C(NR$^{29}$)NR$^{29}$R$^{30}$ and —C(NR$^{29}$)NR$^{29}$R$^{30}$, where each X is independently a halogen; each R$^{29}$ and R$^{30}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl, substituted heteroarylalkyl, —NR$^{31}$R$^{32}$, —C(O)R$^{31}$ or —S(O)$_2$R$^{31}$ or optionally R$^{29}$ and R$^{30}$ together with the atom to which they are both attached form a cycloheteroalkyl or substituted cycloheteroalkyl ring; and R$^{31}$ and R$^{32}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Sulfonic acids derivatives" as used herein are a class of organic acid radicals with the general formula RSO$_3$H or RSO$_3$. An oxygen, suflur, or R moiety can serve as a point of attachment. Sulfonic acid salt derivatives substitute a cationic salt (e.g. Na$^+$, K$^+$, etc.) for the hydrogen on the sulfate group. In various embodiments, the deprotonated sulfonic acid group can be used as the point of attachment to a therapeutic or targeting group, optionally via a linker. Examples of sulfonic acid derivatives and include, but are not limited to, 2-methyl-2-propane-1-sulfonic acid-sodium salt, 2-sulfoethyl methacrylate, 3-phenyl-1-propene-2-sulfonic acid-p-toluidine salt, 3-sulfopropyl acrylate-potassium salt, 3-sulfopropyl methacrylate-potassium salt, ammonium 2-sulfatoethyl methacrylate, styrene sulfonic acid, 4-sodium styrene sulfonate.

"Anhydride derivatives" as used herein refer to a compound or radical having the chemical structure R$_1$C(O)OC(O)R$_2$. The carboxyl groups, optionally after removal of R$_1$ or R$_2$ groups, can be used as the point of attachment to a therapeutic or targeting group, optionally via a linker. Examples of anhydride derivatives include, but are not limited to, acrylic anhydride, methacrylic anhydride, maleic anhydride, and 4-methacryloxyethyl trimellitic anhydride "Hydroxyl derivative" as used herein refers to a compound or radical having the structure ROH. The deprotonated hydroxyl group can be used as the point of attachment to a therapeutic or targeting group, optionally via a linker. Example of hydroxyl derivatives include, but are not limited to, vinyl alcohol, 2-hydroxyethyl acrylate, 2-hydroxyethyl methacrylate, 2-allyl-2-methoxyphenol, divinyl glycol, glycerol monomethacrylate, poly(propylene glycol) monomethacrylate, N-(2-hydroxypropyl)methacrylamide, hydroxymethyldiacetoneacrylamide, poly(ethylene glycol) monomethacrylate, N-methacryloylglycylglycine, N-methacryloylglycyl-DL-phenylalanylleucylglycine, 4-methacryloxy-2-hydroxybenzophenone, 1,1,1-trimethylolpropane diallyl ether, 4-allyl-2-methoxyphenol, hydroxymethyldiacetoneacrylamide, N-methylolacrylamide, and sugar based monomers.

"Amine derivatives" are compound or radicals thereof having a functional group containing at least one nitrogen, and having the structure RNR'R". R, R' and R" in amine derivatives can each independently be any desired substituent, including but not limited to hydrogen, halides, and substituted or unsubstituted alkyl, alkoxy, aryl or acyl groups. "Amide derivatives" as used herein refer to compounds having the structure RC(O)NR'R". The R, R' and R" in amide derivatives can each independently be any desired substituent, including but not limited to hydrogen, halides, and substituted or unsubstituted alkyl, alkoxy, aryl or acyl groups. The amine or amide group can be used as the point of attachment to a therapeutic or targeting group, optionally via a linker. Examples of amines and amides include, but are not limited to, 2-(N,N-diethylamino)ethyl methacrylate, 2-(N,N-diethylamino)ethyl acrylate, N-[2-(N,N-dimethylamino)ethyl]methacrylamide, N-[3-(N,N-dimethylamino)propyl]acrylamide, diallylamine, methacryloyl-L-lysine, 2-(tert-butylamino)ethyl methacrylate, N-(3-aminopropyl)methacrylamide hydrochloride, 3-dimethylaminoneopentyl acrylate, N-(2-hydroxypropyl)methacrylamide, N-methacryloyl tyrosine amide, 2-diisopropylaminoethyl methacrylate, 3-dimethylaminoneopentyl acrylate, 2-aminoethyl methacrylate hydrochloride, hydroxymethyldiacetoneacrylamide, N-(iso-butoxymethyl)methacrylamide and N-methylolacrylamide.

"Silane derivative" as used herein refers to compounds or radicals thereof having at least one substituent having the structure RSiR'R"R'". R, R' and R" can each independently be any desired substituent, including but not limited to hydrogen, alkyl, alkoxy, aryl or acyl groups. The silane group can be used as the point of attachment to a therapeutic or targeting group, optionally via a linker. Examples of silane derivatives include, but are not limited to, 3-methacryloxypropyl trimethoxysilane, vinyltriethoxysilane, 2-(trimethylsiloxy)ethyl methacrylate, 1-(2-trimethylsiloxyethoxy)-1-trimethylsiloxy-2-methylpropene "Phosphate derivatives" as used herein refer to compounds or radicals thereof having at least one compound containing the structure RR'R"PO$_4$. R, R' and R" can each independently be any desired substituent, including but not limited to hydrogen, alkyl, alkoxy, aryl or acyl groups. The phosphate group can be used as the point of attachment to a therapeutic or targeting group, optionally via a linker. Examples of phosphate derivatives include, but are not limited to, monoacryloxyethyl phosphate and bis(2-methacryloxyethyl)phosphate.

"Nitro derivatives" as used herein refer to compounds or radicals thereof having an NO$_2$ group. The nitro group can be used as the point of attachment to a therapeutic or targeting group, optionally via a linker. Examples include, but are not limited to, o-nitrobenzyl methacrylate, methacryloylglycyl-DL-phenylalanyl-L-leucyl-glycine 4-nitrophenyl ester, methacryloylglycyl-L-phenylalanyl-L-leucyl-glycine 4-nitrophenyl ester, N-methacryloylglycylglycine 4-nitrophenyl ester, 4-nitrostyrene "Succinimide derivative" as used herein refers to compounds or radicals thereof having the group

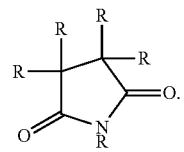

The succinyl R groups can be substituted by any substituent, for example and substituted or unsubstituted alkyl, alcoxy, aryl groups. Typically, the succinimide group is attached to a compound via a covalent bond at the nitrogen. The succinimide group can be used as the point of attachment to a therapeutic or targeting group, optionally via a linker. A succinimide derivative can be a sulfo-containing succinimide derivative. N-acryloxysuccinimide is an exemplary succinimide derivative.

"Halide derivatives" as used herein refer to compounds or radicals thereof having a halide substituent. The halide group can be used as the point of attachment to a therapeutic or targeting group, optionally via a linker. Examples include, but are not limited to, vinyl chloride, 3-chlorostyrene, 2,4,6-tribromophenyl acrylate, 4-chlorophenyl acrylate, 2-bromoethyl acrylate. Non-limiting examples include, but are not limited to, divinylbenzene, ethylene glycol diacrylate, N,N-diallylacrylamide, and allyl methacrylate.

"Morpholine derivatives" as used herein refer to compounds or radicals thereof having the structure:

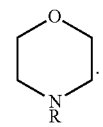

Typically, the amine group serves as the point of attachment to other compounds. The morpholine group can be used as the point of attachment to a therapeutic or targeting group, optionally via a linker. Examples of morpholine derivatives include, but are not limited to, N-acryloylmorpholine, 2-N-morpholinoethyl acrylate and 2-N-morpholinoethyl methacrylate.

"Cyano derivatives" as used herein refer to compounds or radicals thereof having the structure RCN. R can each independently be any desired substituent. The cyano group can be used as the point of attachment to a therapeutic or targeting group, optionally via a linker. Examples of cyano derivatives include, but are not limited to, 2-cyanoethyl acrylate.

"Epoxide derivatives" as used herein refer to compounds or radicals thereof having the following chemical structure:

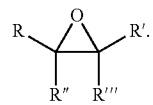

R, R', R", and R'" can each independently be any desired substituent. The epoxide group can be used as the point of attachment to a therapeutic or targeting group, optionally via a linker. Examples of epoxide derivatives include, but are not limited to, glycidyl methacrylate.

"Ester derivatives" as used herein refer to a compound or a radical thereof having the generic chemical structure RC(O)OR'. R and R' can each independently be any desired substituent. The ester group can be used as the point of attachment to a therapeutic or targeting group, optionally via a linker. Examples include, but are not limited to, methyl acrylate, methyl methacrylate, tert-butyl acrylate, tert-butyl methacrylate, vinyl acetate, benzyl acrylate and benzyl methacrylate.

"Ether derivatives" as used herein refer to a compound or a radical thereof having the generic chemical structure R—O—R'. The ether group can be used as the point of attachment to a therapeutic or targeting group, optionally via a linker. Examples include, but are not limited to, methyl vinyl ether, butyl vinyl ether, 2-chloroethyl vinyl ether, cyclohexyl vinyl ether.

"Carbazole derivatives" as used to herein refer to a compound or radical thereof having the structure

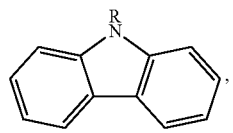

and any substitutions at any site thereof. The carbazole group can be used as the point of attachment to a therapeutic or targeting group, optionally via a linker. Examples of carbazole derivatives include but are not limited to, N-vinylcarbazole.

"Azide derivatives" as used herein refer to a compound or a radical thereof having the structure N=N=N. The azide group can be used as the point of attachment to a therapeutic or targeting group, optionally via a linker. Examples of azide derivatives include, but are not limited to, 2-hydroxy-3-azidopropyl methacrylate, 2-hydroxy-3-azidopropyl acrylate, 3-azidopropyl methacrylate.

The term "maleimide derivative" as referred to herein refers to a compound or a radical thereof having the structure:

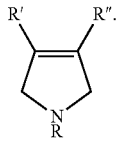

R, R' and R" can each independently be any desired substituent.

The term "thiolate" refers to a compound or radical thereof having a —SR structure, where R can be any desired substituent.

The term "thioether" refers to a compound or radical thereof having the structure R—S—CO—R', where R and R' can each independently be any desired substituent.

The term "thioester" refers to a compound or radical thereof having the structure R—S—CO—R', where R and R' can each independently be any desired substituent.

The term "carboxylate" refers to a compound or radical thereof having the structure RCOO—, where R can be any desired substitutent.

The term "phosphonate" refers to a compound or radical thereof having the structure R—PO(OH)$_2$ or R—PO(OR')$_2$ where R and R' can each independently be any desired substituent.

The term "phosphinate" refers to a compound or radical thereof having the structure OP(OR)R'R" where R, R' and R' can each independently be any desired substituent.

The term "sulphonate" refers to a compound or radical thereof having the structure RSO$_2$O$^-$ where R can be any desired substituent.

The term "sulphate" refers to a compound or radical thereof having the structure RSO$_4$. where R can be any desired substituent.

A "reducing agent" is an element or a compound that reduces another species. Exemplary reducing agents include, but are not limited to, ferrous ion, lithium aluminium hydride (LiAlH$_4$), potassium ferricyanide (K$_3$Fe(CN)$_6$), sodium borohydride (NaBH$_4$), sulfites, hydrazine, diisobutylaluminum hydride (DIBAH), primary amines, and oxalic acid (C$_2$H$_2$O$_4$).

"Treating" or "treatment" of any disease or disorder refers, in some embodiments, to ameliorating the disease or disorder (i.e., arresting or reducing the development of the disease or at least one of the clinical symptoms thereof). In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter), or both. In still other embodiments, "treating" or "treatment" refers to delaying the onset of the disease or disorder.

The term "antibody" refers to a monomeric or multimeric protein comprising one or more polypeptide chains that binds specifically to an antigen. An antibody can be a full length antibody or an antibody fragment.

By "full length antibody" herein is meant the structure that constitutes the natural biological form of an antibody, including variable and constant regions. For example, in most mammals, including humans and mice, the full length antibody of the IgG class is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, CH1 (Cγ1), CH2 (Cγ2), and CH3 (Cγ3). In some mammals, for example in camels and llamas, IgG antibodies may consist of only two heavy chains, each heavy chain comprising a variable domain attached to the Fc region.

"Antibody fragments" are portions of full length antibodies that bind antigens. Specific antibody fragments include, but are not limited to, (i) the Fab fragment consisting of VL, VH, CL and CH1 domains, (ii) the Fd fragment consisting of the VH and CH1 domains, (iii) the Fv fragment consisting of the VL and VH domains of a single antibody; (iv) the dAb fragment (Ward et al., 1989, Nature 341:544-546) which consists of a single variable, (v) isolated CDR regions, (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al., 1988, Science 242:423-426, Huston et al., 1988, Proc. Natl. Acad. Sci. U.S.A. 85:5879-5883), (viii) bispecific single chain Fv dimers (PCT/US92/09965) and (ix) "diabodies" or "triabodies", multivalent or multispecific fragments constructed by gene fusion (Tomlinson et. al., 2000, Methods Enzymol. 326:461-479; WO94/13804; Holliger et al., 1993, Proc. Natl. Acad. Sci. U.S.A. 90:6444-6448). In certain embodiments, antibodies are produced by recombinant DNA techniques. Other examples of antibody formats and architectures are described in Holliger & Hudson, 2006, Nature Biotechnology 23(9):1126-1136, and Carter 2006, Nature Reviews Immunology 6:343-357 and references cited therein, all expressly incorporated by reference. In additional embodiments, antibodies are produced by enzymatic or chemical cleavage of naturally occurring antibodies.

Nanoparticles

The present disclosure is directed to modified gold nanoparticles. The term "nanoparticle" as referred to herein means a particle including gold metal organic framework having at least one special dimension measurable less than a micron in length. Nanoparticles include conventionally known nanoparticles such as nanorods, nanospheres and nanoplatelets. In various embodiments, for example, nanospheres can be a rod, sphere, or any other three dimensional shape. Nanoparticles are generally described, for example, in Burda et al., Chem. Rev. 2005, 105, 1025-1102.

Gold Nanoparticles

Gold nanostructures have architectures which provide tunable optical properties. In various embodiments, gold nanoparticles are configured for optical imaging techniques. For example, the optical and electronic properties can be controlled by controlling the size of the nanoparticle, varying the aspect ratio, or rationally assembling nanorods into a specific shape. Those of skill in the art will understand that the size of the gold nanoparticle can be designed to have specific properties for different applications. For example, the size of the gold nanoparticle can be designed for colorimeric detection, as described in Martin and Mitchell, Anal. Chem. 1998 pp. 332. Additionally, due to their tunable optical properties, multifunctional polymer modified gold nanoparticles can be employed as imaging agents through dark field and confocal microscopy.

Gold nanorods have been used for cancer therapy. Alteration of their shape and size has proven a useful tool to preferentially kill cancer cells through near-infrared lasers and modification with PEG polymers has increased their biocompatibility. Gold nanoparticles may be prepared by methods known in the art, including those disclosed by Burda et al., Chem. Rev. 2005, 105, 1025-1102 and Daniel and Astruc Chem. Rev. 2004, 104, 293-346. Growth methods, including the template, electrochemical, or seeded growth methods, are disclosed by Pérez-Juste et al., Coordination Chemistry Reviews 249 (2005) 1870-1901. Seed particle methods are further described in Murphy et al. J. Phys. Chem. B 2005, 109, 13857-13870. Gold nanoparticles can also be prepared to have specific surface structures by citrate reduction, two phage synthesis and thiol stabilization, sulfur stabilization, and stabilization with other ligands as described by Daniel and Astruc, Chem. Rev. 2004, 104, 293-346.

FIG. 1 depicts TEM images of various exemplary gold nanorod structures.

Forming Initiators on the Nanoparticle Surface

Prior to growing polymers on the surface of Au nanoparticles, the nanoparticle can be treated to form imperfections (or initiators) on the nanoparticle surface that facilitate polymer formation or polymer precursor binding. Initiating gold nanoparticles may be accomplished by methods generally known in the art.

Figure 2:
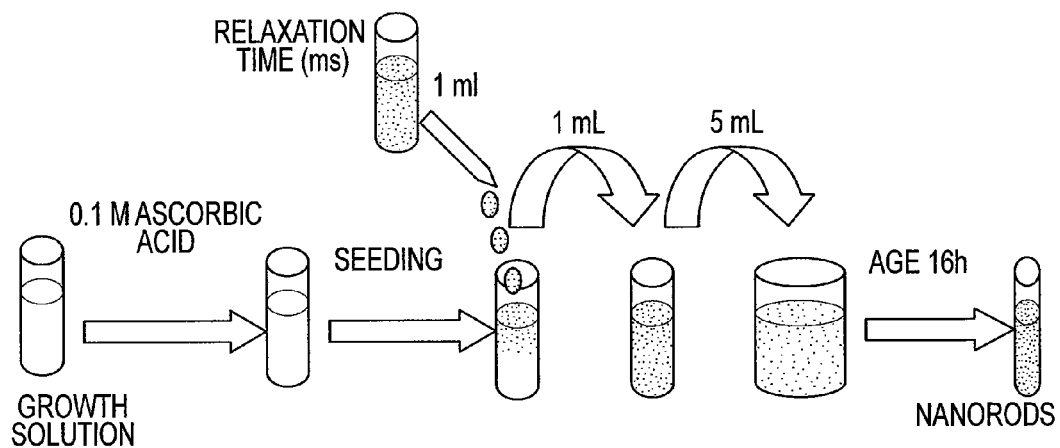
FIG. 2 depicts an exemplary protocol for seeding a gold nanorod.

FIG. 2 depicts an exemplary protocol in which a gold nanorod is seeded as described in Daniel and Astruc, Chem. Rev. 2004. In brief, seeds can be synthesized via the reduction of gold salts with a strong reducing agent (e.g. $NaBH_4$) in presence of capping agent (e.g. citrate). Seeds are added to the metal salt in a weak reducing agent (e.g. ascorbic acid) and surfactant-directing agent (e.g. CTAB). The solution is aged 16 hours, and the nanoparticles are siphoned and purified via centrifugation.

Figure 3:
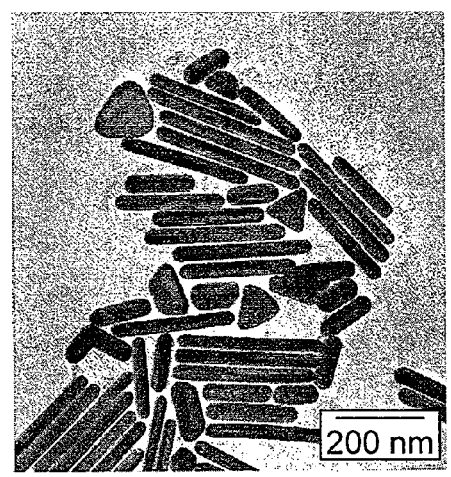
FIG. 3 depicts a group of gold nanorods that have been seeded according to the method depicted in FIG. 2.

FIG. 3 depicts a group of gold nanorods that have been seeded according to the method depicted in FIG. 2.

Polymerization

Polymerization can be performed by any method known in the art. Polymerization methods that can be used are described in Principles of Polymerization, 4th edition (2004) by George Odian, Published by Wiley-Interscience, which is incorporated herein by reference in its entirety. Various methods of polymerization include RAFT, Atom Transfer Radical Polymerization (ATRP), Stable Free Radical Polymerization (SFRP), and conventional free radical polymerization.

Reversible addition-fragmentation chain transfer (RAFT) polymerization operates on the principle of degenerative chain transfer. Without being limited to a particular mechanism, Scheme 1 shows a proposed mechanism for RAFT polymerization. In Scheme I, RAFT polymerization involves a single- or multi-functional chain transfer agent (CTA), such as the compound of formula (I), including dithioesters, trithiocarbonates, xanthates, and dithiocarbamates. The initiator produces a free radical, which subsequently reacts with a polymerizable monomer. The monomer radical reacts with other monomers and propagates to form a chain, Pn*, which can react with the CTA. The CTA can fragment, either forming R*, which will react with another monomer that will form a new chain $P_m^*$ or $P_n^*$, which will continue to propagate. In theory, propagation to the $P_m^*$ and $P_n^*$ will continue until no monomer is left or a termination step occurs. After the first polymerization has finished, in particular circumstances, a second monomer can be added to the system to form a block copolymer.

Scheme 1

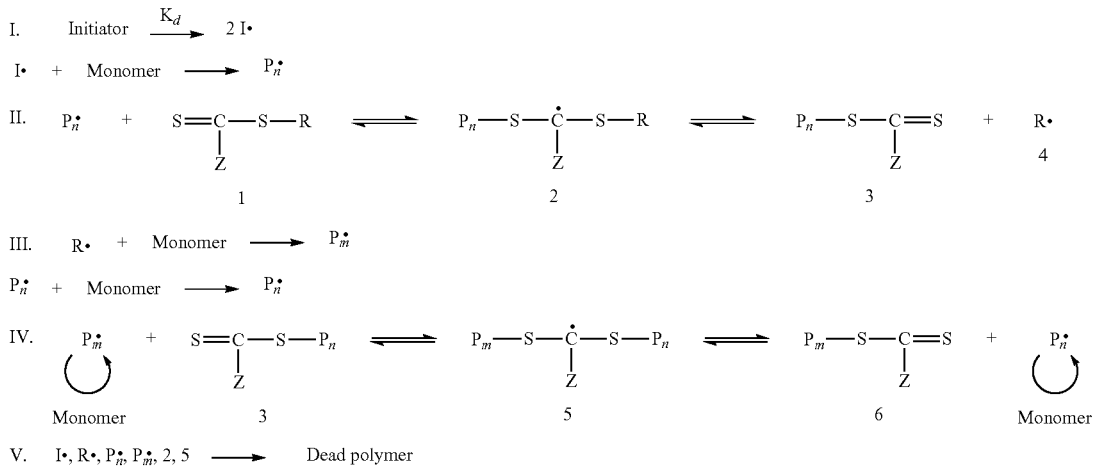

RAFT polymerization involves a similar mechanism as traditional free radical polymerization systems, with the difference of a purposely added CTA. Addition of a growing chain to a macro-CTA yields an intermediate radical, which can fragment to either the initial reactants or a new active chain. With a high chain transfer constant and the addition of a high concentration of CTA relative to conventional initiator, synthesis of polymer with a high degree of chain-end functionality and with well defined molecular weight properties is obtained. In certain embodiments, a dithioester, xanthate, dithiocarbamate, or trithiocarbonate group is reduced to produce a thiol or thiolate, which has provided a successful route of RAFT polymer attachment to gold surfaces.

In particular embodiments, RAFT polymerization is used to produce a variety of well-defined, novel polymers that either are polymerized from the surface of the nanoparticles, or are polymerized and then attached to the surface of the nanoparticle. RAFT polymerization shows great promise in the synthesis of multifunctional polymers due to the versatility of monomer selection and polymerization conditions, along with the ability to produce well-defined, narrow polydispersity polymers with both simple and complex architectures. The flexibility of RAFT polymerizations makes it an ideal candidate to produce well-defined polymer structures with a high degree of functionality capable of providing increased therapeutic/targeting agent loading and loading efficiency. For example, RAFT can be successfully used to produce well-defined activated biocopolymer constructs with N-acryloxysuccinimide (NAOS) pendant functionalities. The succinimide side groups have allowed covalent conjugation of bioactive agents such as fluorescent tags, nucleotides, peptides, and antibodies. Incorporation of NAOS into copolymers provides a route of manipulating loading efficiency and stability of bioactive agents. Additional tailoring of the copolymer conjugate system with tumor targeting or therapeutic agents allows specific localization and treatment to be achieved increasing in vivo performance.

Polymers synthesized by RAFT include chain transfer agents (CTAs). As used herein, a RAFT chain transfer agent is defined as having the chemical structure of Formula (V):

CTAs agents possessing the thiocarbonylthio moiety, impart reactivity to free-radical polymerization due to the facile nature of radical addition to C=S bonds which contributes to faster chain equilibration in the chain transfer step. The transfer constants of RAFT CTAs depend on the Z and R substituents. In certain embodiments, the Z group is a free radical stabilizing species to ensure rapid addition across the C=S bond.

In certain embodiments, the R group is chosen so that it possesses an equal or greater ability to leave as compared to the addition species. It is also of importance that the R group be able to reinitiate the polymerization after fragmentation. In certain embodiments, R can fragment from the intermediate quickly and is able to re-initiate polymerization effectively.

Exemplary CTAs include, but are not limited to, cumyl dithiobenzoate (CDTB) and S-1-Dodecyl-S'-(α,α'-dimethyl-α"-acetic acid)trithiocarbonate (DATC).

Grafting Polymers and Polymer Precursors to Nanoparticles

In certain aspects, polymers can be grafted to the gold nanoparticles after polymerization. Desired choice of CTA structures of formula (I) allows for control of the polymerization. The Z group activates the thio-carbonyl (C=S) group for radical addition and allows for the radical intermediate to be stabilized in the transition state.

Schemes 2 and 3 show grafting trithiocarbonate and dithioester RAFT agents to the surface of a gold nanoparticle with or without the use of a reducing agent. Scheme 2 shows first RAFT polymerization of the alkene in the presence of the trithiocarbonate, and Scheme 3 shows a first step of RAFT polymerization of the alkene in the presence of the dithioester.

The RAFT polymer is grafted to the surface of the nanoparticle. Without being limited to any particular mechanism, the nanoparticle is covalently grafted to the nanoparticle surface. The reduced polymer is covalently grafted to the nanoparticle.

Scheme 2

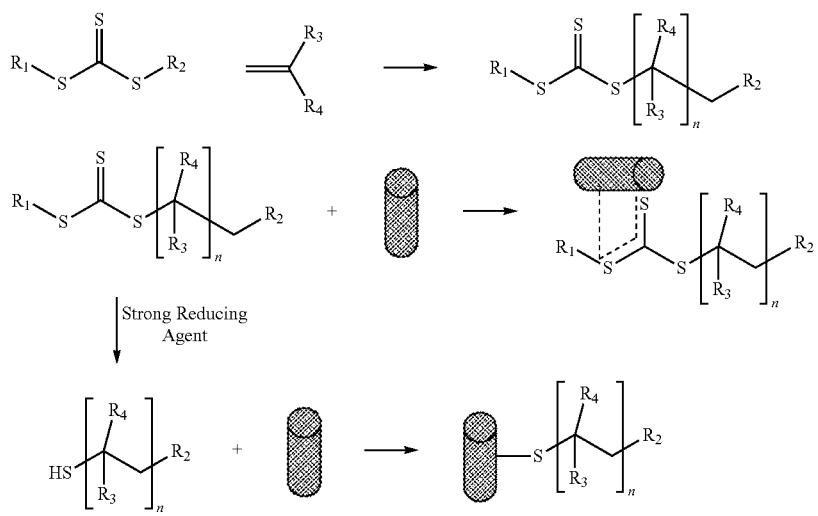

Scheme 3

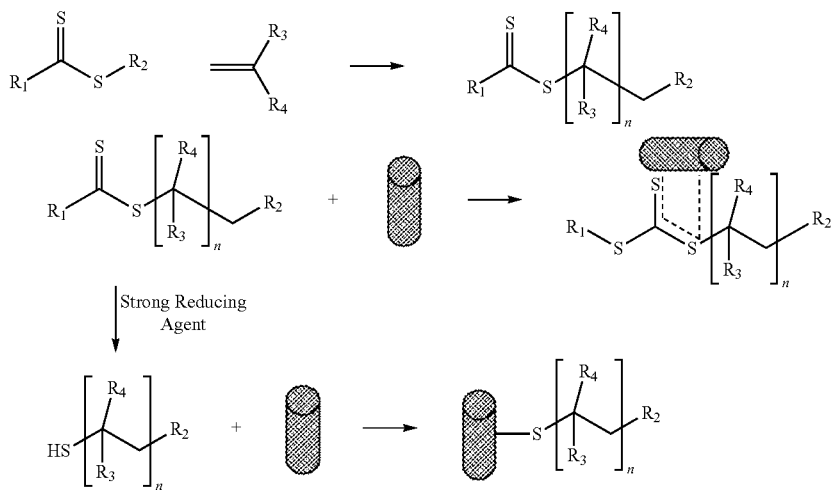

In Schemes 2 and 3, $R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

Specific examples of RAFT polymers attached to the surface of the gold particles after polymerization is depicted in Schemes 4 and 5 below.

Scheme 4 depicts a method of attaching a derivatized polymer to a gold nanoparticle after reduction of the trithiocarbonate to produce a gold nanoparticle conjugate.

Scheme 4

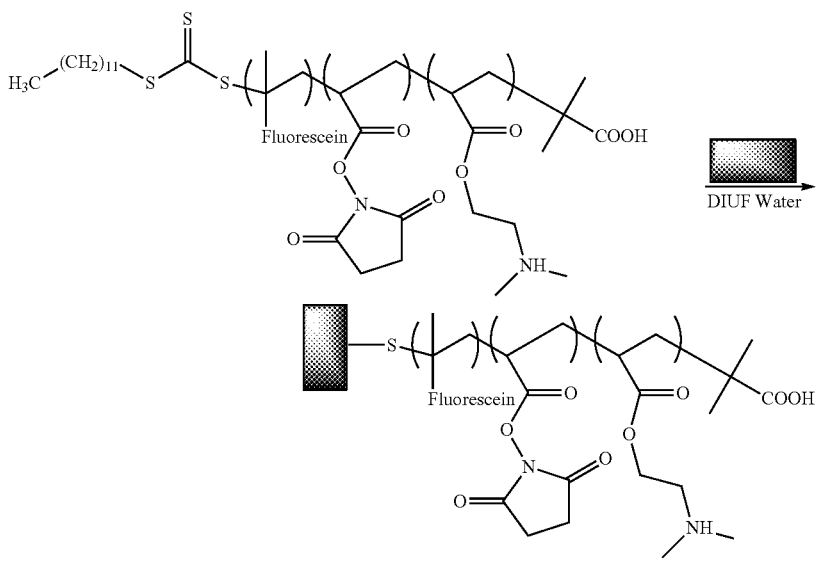

Grafting from Nanoparticles

In the two examples of generalized RAFT polymerization described above in Schemes 2 and 3, as well as the specific example in Scheme 4, polymerization occurs prior to grafting to the gold nanoparticle surface (i.e. "grafting to" the nanoparticle surface).

Alternatively, the RAFT polymerization may be accomplished after grafting a polymer precursor, initiator, or CTA to the nanoparticle surface. Scheme 5 depicts attachment of a CTA to a surface-bound RAFT polymerization. In brief, a polymer precursor is grafted to the surface of the nanoparticle. A CTA is attached to the terminus of the polymer precursor in Step 1. RAFT polymerization is then accomplished in Step 2 directly from the surface of the gold nanoparticle, as described, for example, in Rowe-Konopacki, M. D. and Boyes, S. G. *Synthesis of Surface Initiated Diblock Copolymer Brushes from Flat Silicon Substrates Utilizing the RAFT Polymerization Technique. Macromolecules,* 40 (4) 879-888, 2007, and Rowe, M. D.; Hammer, B. A. G.; Boyes, S. G. *Synthesis of Surface-Initiated Stimuli-Responsive Diblock Copolymer Brushes Utilizing a Combination of ATRP and RAFT Polymerization Techniques. Macromolecules,* 41 (12), 4147-4157, 2008.

Scheme 5

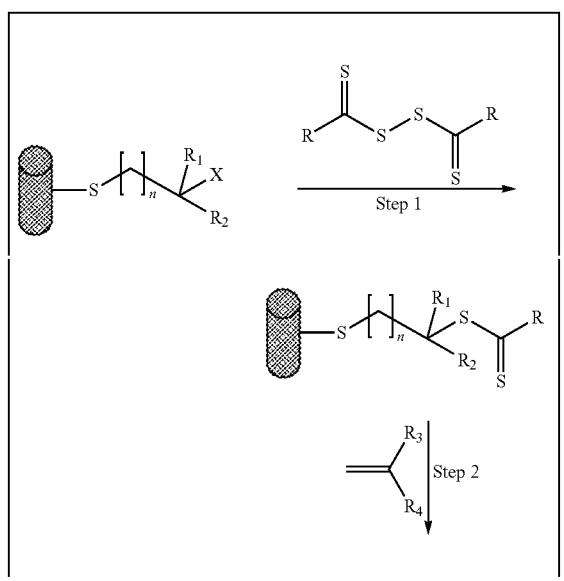

-continued

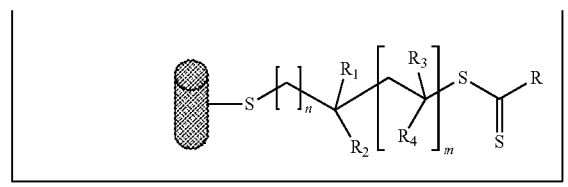

In Scheme 5, n is an integer, and X, R, $R_1$, $R_2$, $R_3$ and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy. In certain embodiments, X is a halide such as fluorine, bromine, chlorine and iodine. A specific example of the reaction of Scheme 5 is depicted in Scheme 6.

Scheme 6

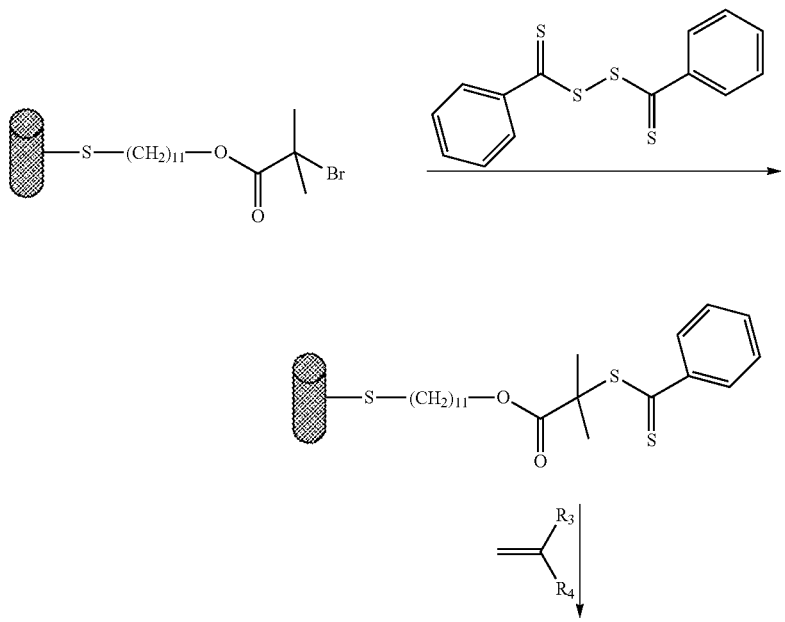

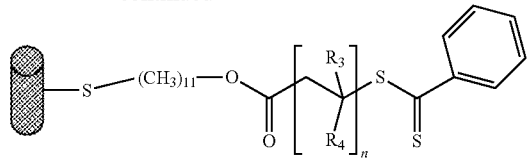

R₃ and R₄ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

Figure 11:
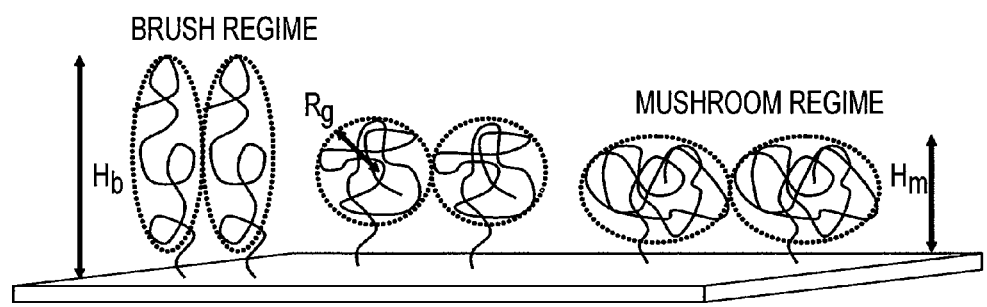
FIG. 11 depicts the mushroom to brush spatial transition of polymers at a surface.
Figure 12:
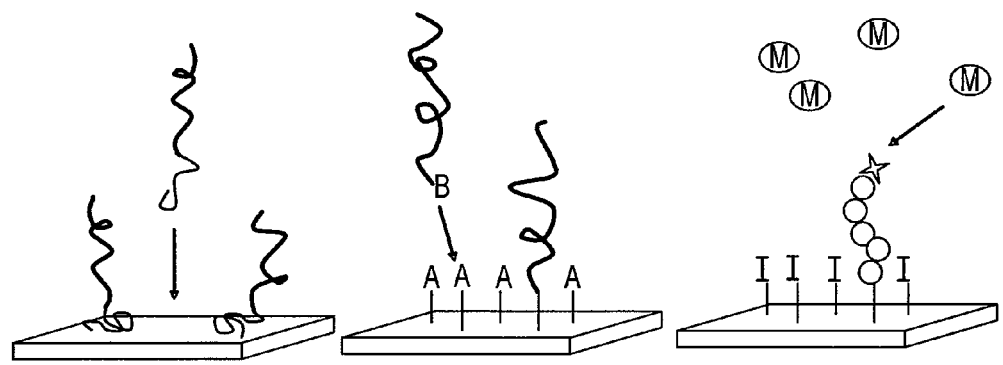
FIG. 12 depicts generating a polymer by grafting a polymer from a polymer precursor M at the surface of the bound polymer.

Grafting from the surface of the nanoparticle as depicted above allows formation of a "brush" configuration of polymers. With reference to FIG. 11, polymers attached to a gold surface can be spaced differently on a surface. Without wishing to be held to a specific theory or mechanism of action, the accessibility of the therapeutic agents and targeting agents to the surrounding environment can be at least partially controlled by how closely together the polymers are spaced on the surface of the nanoparticle. When the distance between the polymers is greater than the length of the polymer, the polymers adopt a "mushroom" configuration in which the entirety of the polymer can be accessible to surrounding environment, including the binding site of a targeting agent or therapeutic agent attached to the polymer. Conversely, when the distance between the polymer chains is shorter than the attached polymer, the polymers have a brush conformation, in which the terminal portions of the polymer are accessible to the surrounding environment. If the therapeutic and/or targeting agents are attached to the terminus of the polymers arranged in a "brush" conformation, then the therapeutic and/or targeting agents can be accessible to the surrounding environment.

Desired polymer configuration on the surface can be achieved by growing the polymers from the surface of the nanoparticle. In certain aspects, the polymerization is initiated directly from substrate via immobilized initiators. The brush polymer conformation can be achieved by forming the polymer from the nanoparticle surface, or alternatively by utilizing separately or combining atom transfer radical polymerization (ATRP) and RAFT polymerization. Growing the polymers from the surface allows immobilized polymerization initiators to be tailored for a wide range of polymerization techniques and substrates.

In particular, synthesizing polymer brushes requires control of the polymer molecular weight (i.e. brush thickness), narrow polydispersities and control of the composition. In the two examples of generalized RAFT polymerization described above in Schemes 6 and 7, polymerization occurs prior to grafting to the gold nanoparticle surface (i.e. "grafting to" the nanoparticle surface).

Functional Groups

Functional groups are groups that can be covalently linked to the polymer and covalently linked to the therapeutic or targeting agents, and/or bonded to the nanoparticles. The functional groups include any group that can be reacted with another compound to form a covalent linkage between the compound and the polymer extending from the nanoparticle. Exemplary functional groups can include carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives. The functional groups can be substituted or unsubstituted, as described herein.

Functional groups can be attached to the polymer during polymerization as depicted herein.

Alternatively, functional groups can be attached to the polymer backbone via a linker. The term "linker" as used herein refers to any chemical structure that can be placed between the polymer and functional group. For example, linkers include a group including alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxyalkyl groups. In various non-limited exemplary embodiments, the groups can be from C1 to C10, C20, or C30.

In various embodiments, the linker can include a conjugated bond, preferably selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly certain bonds are acetylene, alkene, amide, and substituted derivatives of these three, and azo. The linker could also be carbonyl, or a heteroatom moiety, wherein the heteroatom is selected from oxygen, sulfur, nitrogen, silicon or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). The linker could also be a peptidyl spacer such as Gly-Phe-Leu-Gly.

Therapeutic Agents and Targeting Agents

Figure 13:
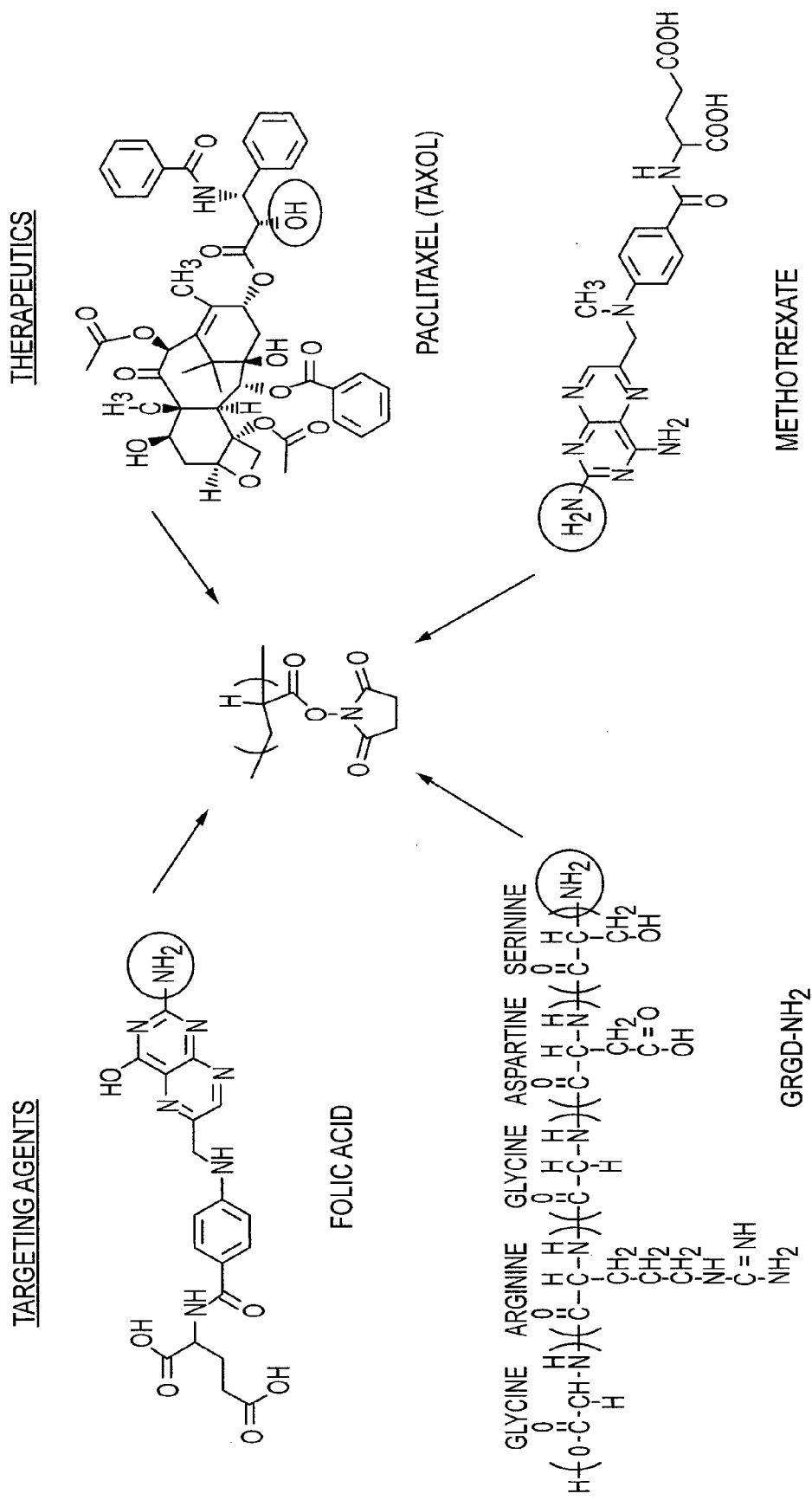
FIG. 13 depicts exemplary targeting molecules (folic acid or an RGD sequence) and exemplary therapeutic agents (the cancer therapeutics paclitaxel or methotrexate) binding to a functionalized polymer grafted to a nanoparticle.

Targeting agents and therapeutic agents can be covalently attached to the polymer. FIG. 13 shows exemplary targeting molecules (folic acid or an RGD sequence) and exemplary therapeutic agents (the cancer therapeutics paclitaxel or methotrexate) binding to a functionalized polymer grafted to a nanoparticle. The functional groups attach to the polymer backbone by reaction with the succinimide functional group. Conjugation of therapeutic, targeting, and imaging agents to the copolymer provides a multifaceted system, which has potential in decreasing toxicity while increasing efficacy of the drug due to directed treatment through directed targeting with the ability to image through optical, magnetic resonance, or computer tomography.

It will be understood by those of skill in the art that various targeting agents or therapeutic agents can be selected for attachment to functional groups. Further, it will be understood that a linker can be placed between the functional groups and the targeting agents and therapeutic agents. The linker can be cleavable or non-cleavable. For example, in certain instances therapeutic agents can be cleavable. In certain instances, diagnostic agents can be non-cleavable.

Targeting agents are compounds with a specific affinity for a target compound, such as a cell surface epitope associated with a specific disease state. Targeting agents may be attached to a nanoparticle surface to allow targeting of the nanoparticle to a specific target. Non-limiting examples of targeting agents include an amino acid sequence including the RGD peptide, an NGR peptide, folate, Transferrin, GM-CSF, Galactosamine, peptide linkers including growth factor receptors (e.g. IGF-1R, MET, EGFR), antibodies and antibody fragments including anti-VEGFR, Anti-ERBB2, Anti-tenascin, Anti-CEA, Anti-MUC1, Anti-TAG72, mutagenic bacterial strains, and fatty acids.

In various embodiments, targeting agents can be chosen for the different ways in which they interact with tumors. For example, when the targeting agent folic acid is taken into the cells by the folate receptors, RGD receptors are expressed on the surface of the cells, resulting in the nanostructures localizing to the cell surface. The folate receptor is known to be over expressed in cancer cells in the case of epithelial malignancies, such as ovarian, colorectal, and breast cancer, whereas in most normal tissue it is expressed in very low levels.

Therapeutic agents include any therapeutic compounds that are capable of preventing or treating a disease in a patient. Numerous therapeutic agents are known in the art. Non-limiting examples of therapeutic agents include doxorubicin, paclitaxel, methotrexate, cisplatin, camptothecin, vinblastine, aspartic acid analogues, and short interfering ribonucleic acid (siRNA) molecules.

Therapeutic agents and targeting agents can be covalently attached to the polymer by RAFT synthesis. The therapeutic agent or targeting agent is configured to be added to the RAFT polymer during polymerization. As such the therapeutic agent and targeting agent can be linked directly to the RAFT polymer. Those of skill in the art will recognize that a linker can be added between the therapeutic agent or targeting agent and the polymer.

Alternatively, therapeutic agents and targeting agents are linked to the polymer via a functional group as described above. Those of skill in the art will recognize that a linker can be added between the therapeutic agent or targeting agent and the polymer.

Multifunctional synthesis of compounds can be accomplished by RAFT polymerization as depicted in the example of Scheme 7.

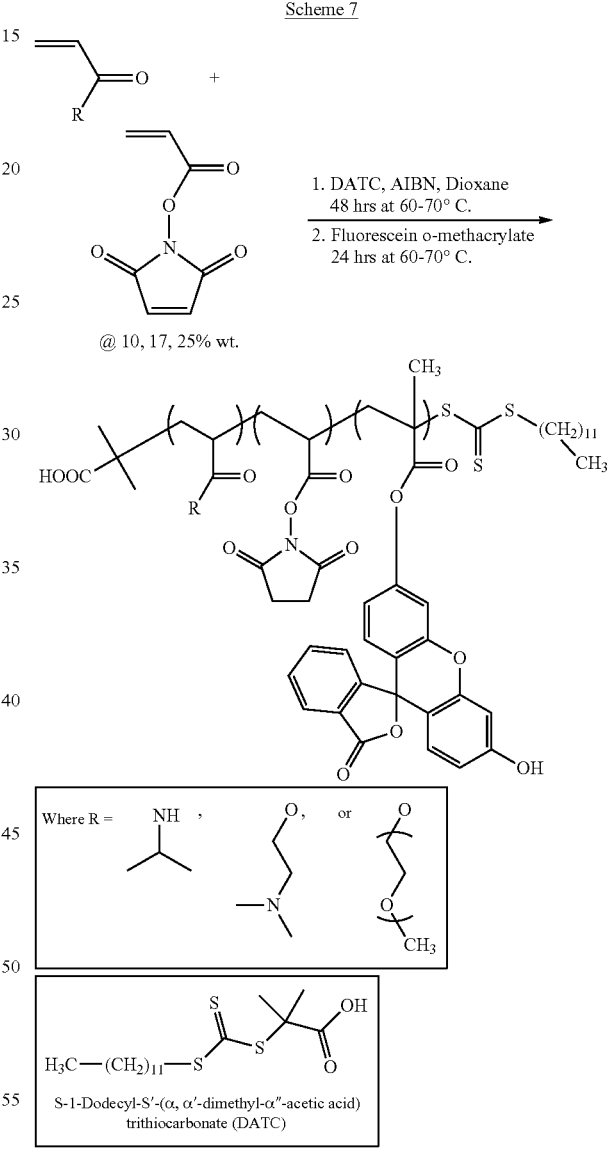

In this embodiment, a succinimide group can be used to attach a functional group to the nanoparticle. An example of biocompatible copolymers containing functional N-acryloyloxysuccinimide (NAOS) monomer units can also be synthesized via RAFT polymerization. A range of copolymer backbones can be used, including, but not limited to, N-isopropylacrylamide (NIPAM), N,N-dimethylaminoethyl acrylate (DMAEA), and poly(ethylene glycol)methyl ether acrylate (PEGMEA). The addition of NAOS into the copolymer backbones has been achieved at a range of weight percents as a means of attachment. The copolymers were synthesized utilizing the well-known trithiocarbonate DATC in dioxane at 60 or 70 degrees, with a fluorescein monomer incorporated near the end of the polymerization. The polymers were characterized via both proton NMR and GPC.

In various embodiments, unreacted succinimide groups can further be converted to non-bioactive groups to reduce in vivo side reactions.

In Scheme 8, a folic acid targeting agent is attached to the succinimide functional group.

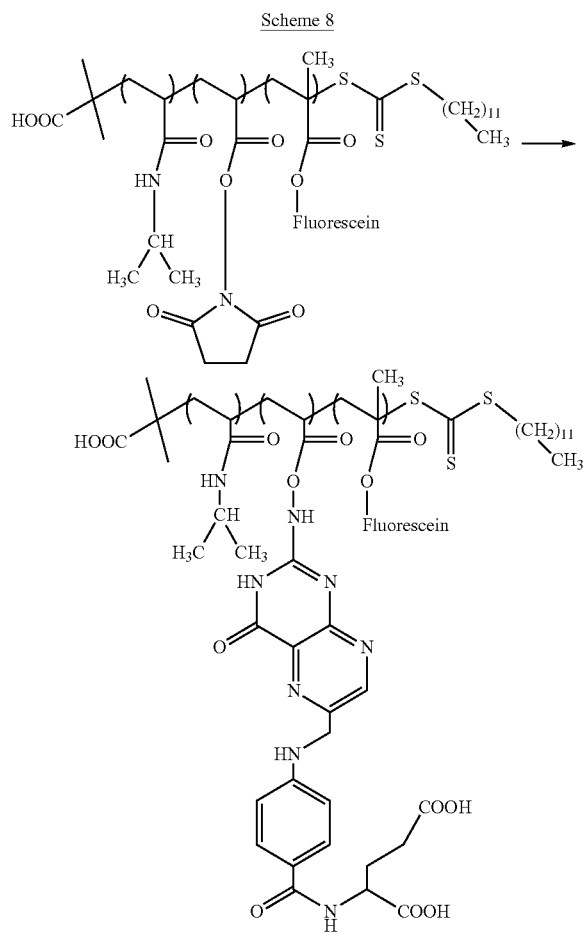

Figure 10A:
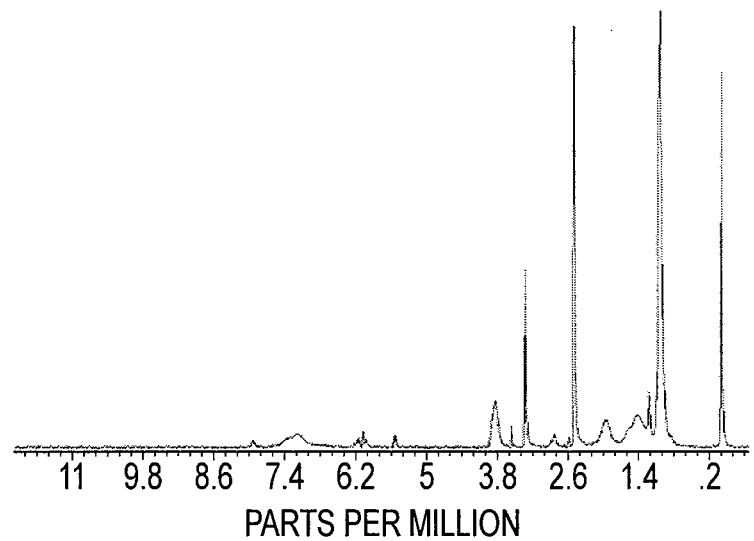
FIG. 10a depicts a $^1$H NMR spectrum of PNIPAM-co-PNAOS-co-PFMA copolymer.
Figure 10B:
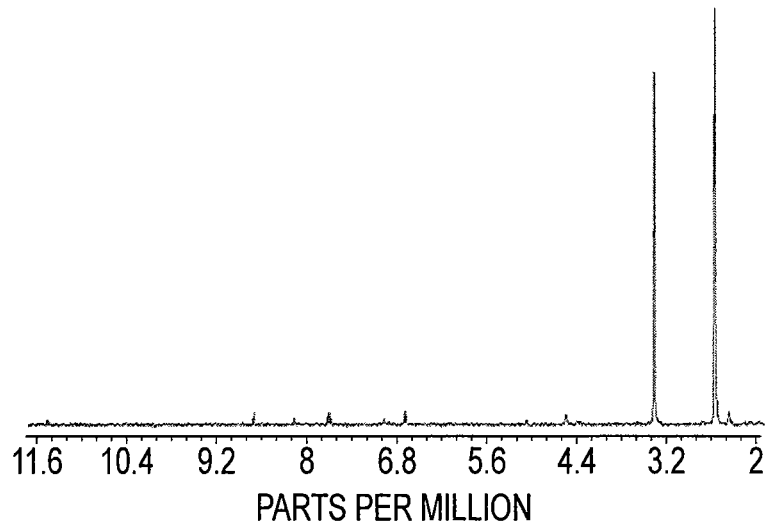
FIG. 10b depicts a $^1$H NMR spectrum of folic acid.
Figure 10C:
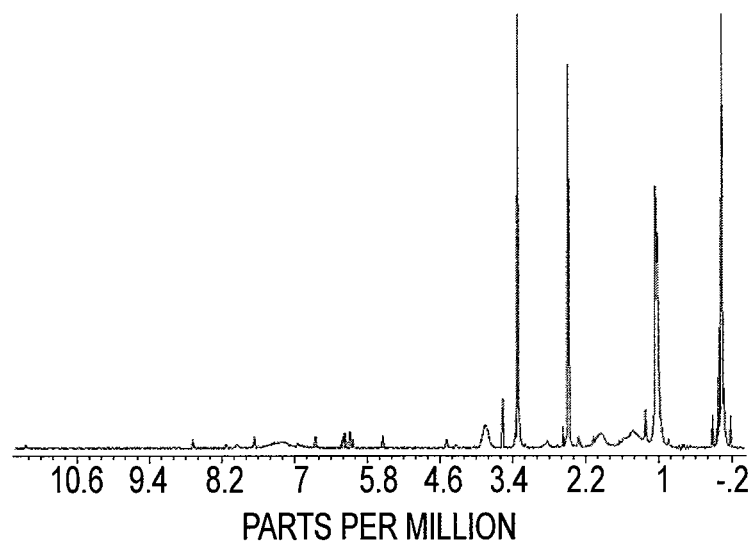
FIG. 10c depicts a $^1$H NMR spectrum of PNIPAM copolymer reacted with folic acid.

FIG. 10a depicts a $^1$H NMR spectrum of PNIPAM-co-PNAOS-co-PFMA copolymer. FIG. 10b depicts a $^1$H NMR spectrum of folic acid. FIG. 10c depicts a $^1$H NMR spectrum of PNIPAM copolymer reacted with folic acid.

Other Methods

Aside from the in vivo diagnosis and treatment of cancer, with attachment of appropriate therapeutics and/or targeting moieties, the invention maybe used for a wide variety of different drug delivery applications, such as gene therapy, imaging applications, such as vascular imaging, and even in external molecular detection devices, such as microarrays and assays. The primary industry interested in the invention would be pharmaceutical companies. While these applications have been mentioned specifically there may be many more applications that the inventors have not considered or are yet to be thought of for the invention.

EXAMPLES

The following examples are intended to be exemplary, and not limit, the present disclosure.

Example 1

Figure 4:
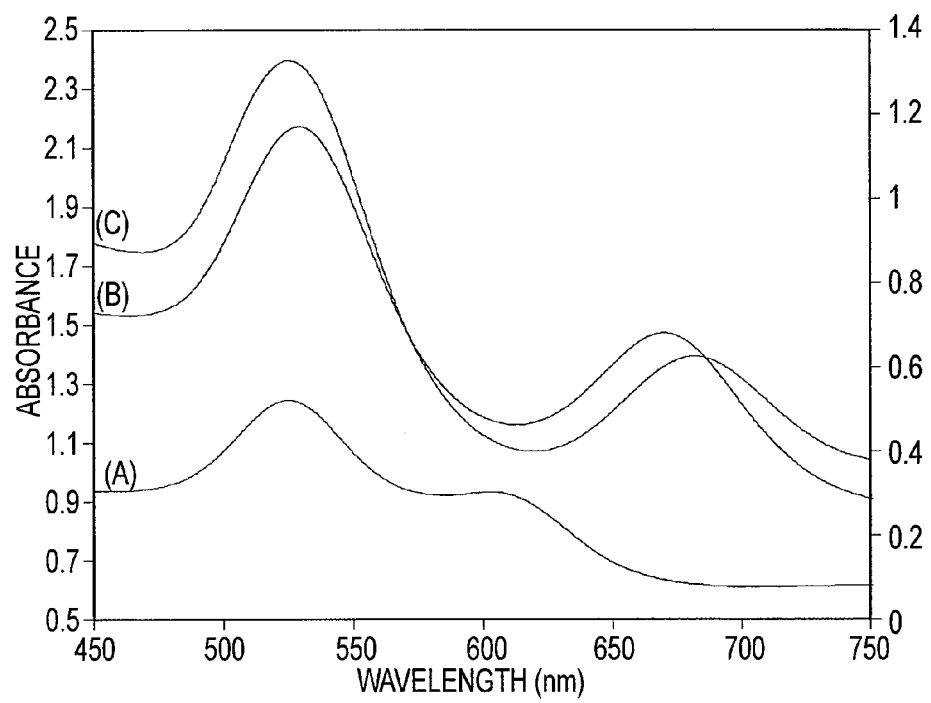
FIG. 4 depicts a comparison absorbance spectrum of A) gold nanorods, B) gold nanorods modified with the strong reducing agent sodium borohydride and poly(acrylic acid) (PAA) and C) gold nanorods modified with PAA and without sodium borohydride.

FIG. 4 depicts a comparison absorbance spectrum of A) gold nanorods, B) gold nanorods modified with the strong reducing agent sodium borohydride and poly(acrylic acid) (PAA) and C) gold nanorods modified with PAA and without sodium borohydride. In this case the peak of most interest is the peak center around 530 nm which is due to the transverse surface plasmon band of the gold nanorods. Murphy and co-workers have shown that red-shifts in this peak an indicative of changes in the local refractive index around the rods, as occurs when polymer is adsorbed to the surface. Furthermore, the peak wavelength shift is highly sensitive to the amount of material adsorbed to the surface, thus UV-vis spectroscopy is a useful tool in monitoring the coating of the gold nanorods with the RAFT polymers.

Figure 5A:
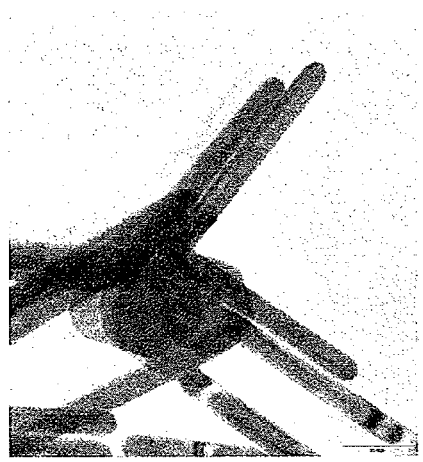
FIGS. 5a and 5b depict TEM images of gold nanorod modified by PAA after treatment with sodium borohydride and without sodium borohydride.
Figure 5B:
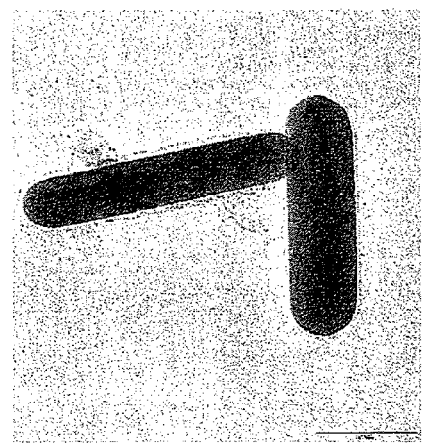

There are three curves in this spectrum. The first of these is the red curve which is the absorption spectrum for the plain, washed gold nanorods, with a maximum around 526 nm. Upon coating the nanorods with RAFT generated PAA that has been reduced with NaBH (the red curve), we see an increase in the maximum absorption to 531 nm, which is consistent with adsorption of PAA to the surface of the gold nanorods. The thickness as determined by TEM was approximately 14 nm. FIGS. 5a and 5b depict TEM images of gold nanorod modified by PAA after treatment with sodium borohydride and without sodium borohydride.

Example 2

Figure 6:
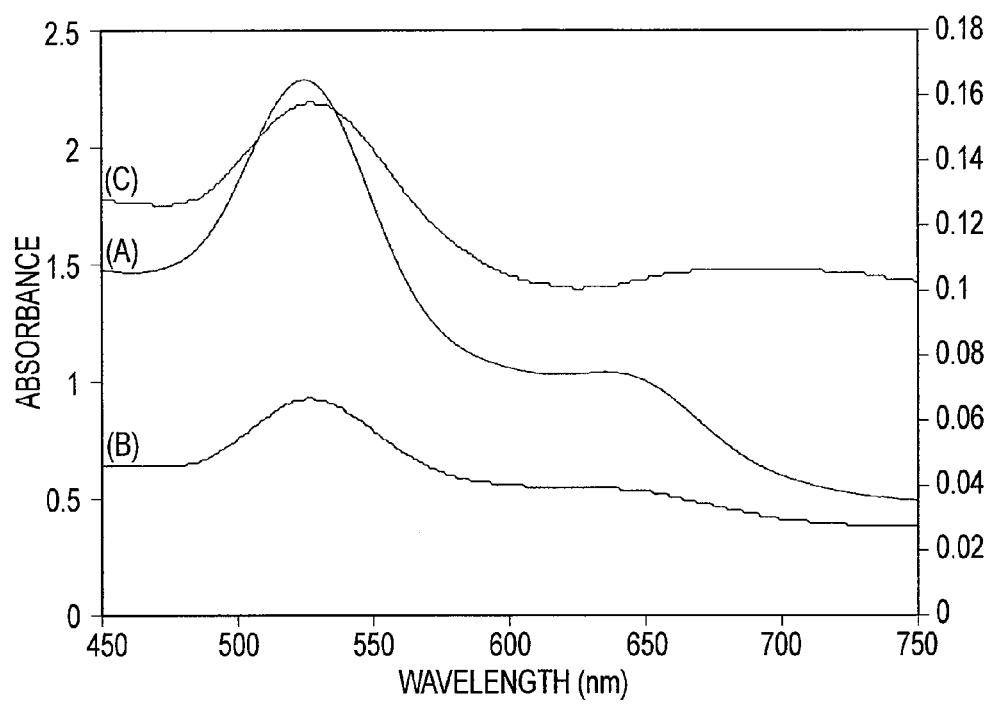
FIG. 6 depicts a comparison absorbance spectrum of A) gold nanorods, B) gold nanorods modified with the strong reducing agent sodium borohydride and (PMMA)-b-poly(2-(dimethylamino)ethyl methacrylate) (PDMAEMA), and C) gold nanorods modified with PDMAEMA and without sodium borohydride.

FIG. 6 depicts a comparison absorbance spectrum of A) gold nanorods, B) gold nanorods modified with the strong reducing agent sodium borohydride and (PMMA)-b-poly(2-(dimethylamino)ethyl methacrylate), and C) gold nanorods modified with PDMAEMA and without sodium borohydride. The absorption maximum for the transverse surface plasmon band of the ungrafted nanorods occurs at a wavelength of 526 nm. Upon coating the gold nanorods with PDMAEMA there is a small red shift in the transverse surface plasmon band of 528 nm when reducing agent was used and 529 nm when it was not used. The increase in wavelength seen upon coating the nanorods with the PDMAEMA relates closely to the average thickness of the PDMAEMA surrounding the nanorods, which is approximately 3 nm, as determined by TEM, in both cases. This corresponds well with the observations of Gole and Murphy, who demonstrated that the nm increase in the wavelength of the transverse surface plasmon band matched the nm thickness of polyelectrolyte adsorbed to the surface of gold nanorods. It should also be mentioned that there appears to be little, if any, broadening of the surface plasmon band peak, which indicates that aggregation upon grafting of the polymer to the surface of the nanorods does not occur.

Figure 7A:
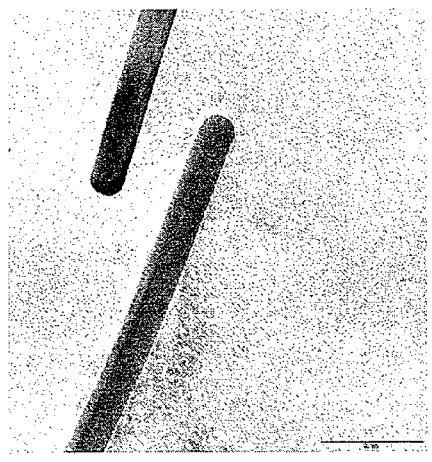
FIGS. 7a and 7b depict TEM images of a gold nanorod modified by poly(2-(dimethylamino)ethyl methacrylate) (PDMAEMA) after treatment with sodium borohydride and without sodium borohydride.
Figure 7B:
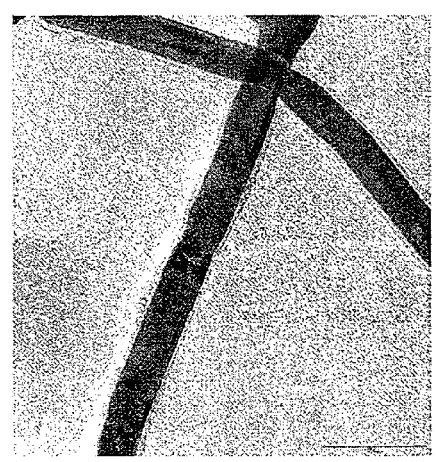

FIGS. 7a and 7b depict TEM images of a gold nanorod modified by PDMAEMA after treatment with sodium borohydride and without sodium borohydride.

Example 3

Figure 8:
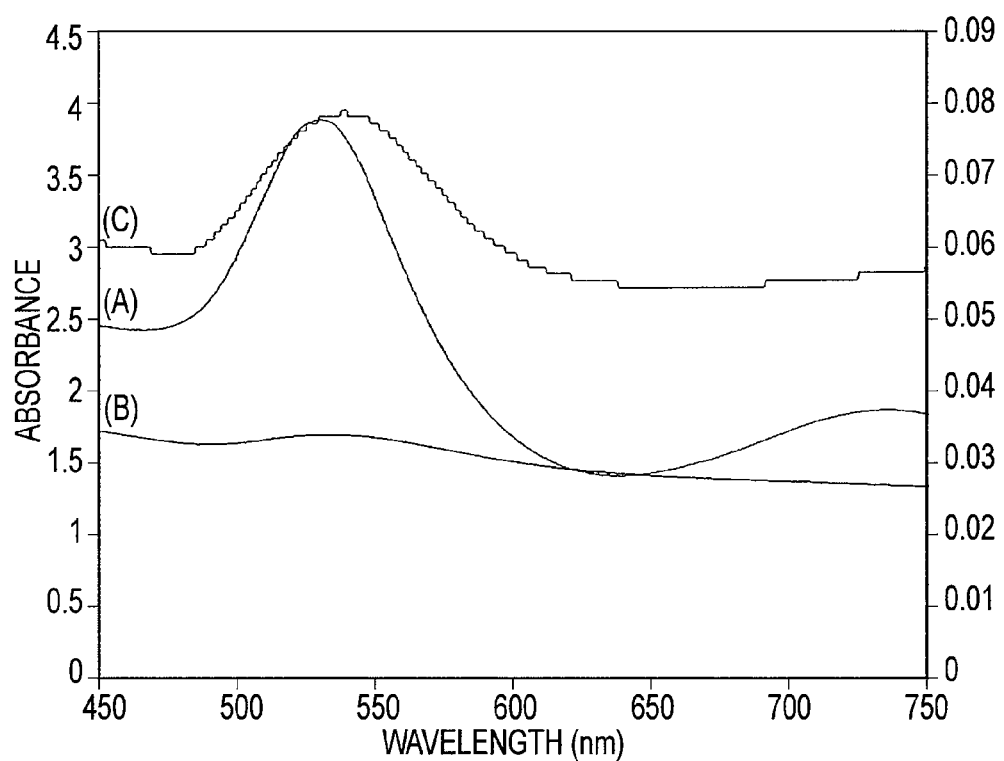
FIG. 8 depicts a comparison absorbance spectrum of A) gold nanorods, B) gold nanorods modified with the strong reducing agent sodium borohydride and polystyrene (PS) and C) gold nanorods modified with PS and without sodium borohydride.

FIG. 8 depicts a comparison absorbance spectrum of A) gold nanorods, B) gold nanorods modified with the strong reducing agent sodium borohydride and polystyrene (PS) and C) gold nanorods modified with PS and without sodium borohydride. TEM micrographs demonstrate that PS is grafted to the surface of the gold nanorods regardless whether reducing agent is used or not. The TEM images indicates an average PS thickness of 3 nm surrounding the nanorod when lithium aluminium hydride (LiAlH$_4$) reducing agent is used versus an 8 nm thickness found when it is not used. UV-Visible spectroscopy was used to verify a red-shift in the transverse surface plasmon band maxima for the samples.

The uncoated purified gold nanorods show an absorption maximum of 531 nm when RAFT generated PS is grafted to the surface. The absorption maxima shift upward to 534 nm when the LiAlH$_4$ reducing agent was used and to 540 nm when no reducing agent was used. The shifts in the absorption maxima for the transverse surface plasmon band correspond closely to the nm thicknesses seen in the TEM images. There also appears to be little to no peak broadening of the surface absorption maxima, suggesting that aggregation is not occurring.

Figure 9A:
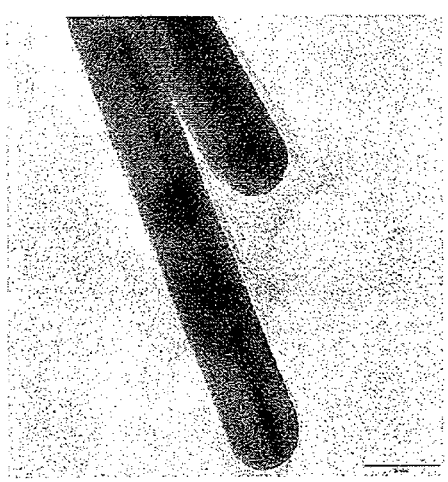
FIGS. 9a and 9b depict TEM images of a gold nanorod modified by PDMAEMA after treatment with sodium borohydride and without sodium borohydride.
Figure 9B:
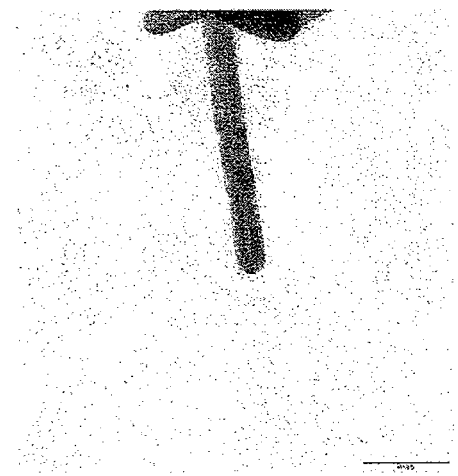

FIGS. 9a and 9b show TEM images of a gold nanorod modified by PDMAEMA after treatment with sodium borohydride and without sodium borohydride.

Example 4

Gold nanorods were synthesized via a three-step seed-mediated approach, providing a good concentration of nanorods with an average length of 300 nm and average diameter of 25 nm. Gold nanorods have been successfully modified using the PNIPAM-co-PNAOS(@25% wt)-co-PFMA copolymer synthesized via RAFT polymerization, where the trithiocarbonate end groups were utilized for immobilization of chains onto the gold nanorod surfaces. Transmission electron microscopy (TEM) images confirm the formation of a relatively uniform film around the entirety of the gold nanorod structure with an average thickness of 6 nm. In combination with TEM, UV-Vis was employed to characterize the virgin nanoparticles. The gold nanorods showed two main absorption maxima, the first at ~525 nm and are attributed to the transverse surface plasmon resonance absorption band. The second at a higher wavelength characteristic of the longitudinal surface plasmon band. UV-Vis verifies immobilization with a comparative red shift in the absorption maxima of the transverse surface plasmon from 520 nm to 527 nm. Additionally, the 7 nm red shift in the UV-Vis directly correlates with the thickness of the polymer coating seen in TEM. The succinimide functionality has been subsequently modified through condensation reactions to attach an assortment of tumor targeting and/or therapeutic agents, such as folic acid, GRGD sequences, Paclitaxel, and Methotrexate. For example, the PNIPAM-co-PNAOS(@25% wt)-co-PFMA was modified by the addition of folic acid through a condensation reaction with the NAOS functionality and a readily accessible primary amine of folic acid. Folic acid has been shown to specifically target over-expressed folate receptors on the periphery of epithelial malignant cancer cells, such as ovarian, colorectal, and breast cancer cells.

Example 5

The ability of nanoparticles to inhibit in vitro was measured. A range of samples including virgin gold nanorods, PNIPAM-co-PNAOS(25% wt)-co-PFMA, PDMAEA-co-PNAOS(25% wt)-co-PFMA, and PPEGMEA-co-PNAOS(@17%)-co-PFMA copolymers, along with gold nanorods modified with PNIPAM-co-PNAOS-co-PFMA copolymer have been studied. Canine osteosarcoma cells were initially used as a proof of concept study and the systems were incubated at physiological temperature, 37° C. for 72 hours in a 5% $CO_2$ atmosphere. Preliminary growth inhibition curves for nanoparticles, unmodified polymers, and polymer modified nanoparticles confirm that none of the compounds show a significant anti-proliferative or cytotoxic effect on the incubated cancer cells.

A range of therapeutic agents and targeting agents were tested for efficacy following post-polymerization covalent attachment of the PNIPAM-co-PNAOS(@25% wt)-co-PFMA copolymer with the agents. Tested therapeutic agents included Paclitaxel and Methotrexate. Targeting agents include folic acid and GRGD sequences. Samples were incubated with CTAC and FITZ at physiological temperature for 4, 24, and 72 hours in a 5% $CO_2$ atmosphere. These cells lines chosen based on their susceptibility to the therapeutic agents being tested, along with targeting ability through the GRGD sequences.

Applicants further note that the compounds and methods disclosed herein include those compounds cited in U.S. 2007/0123670 to McCormick et al., which is incorporated herein by reference in its entirety.

All references cited herein are incorporated herein by reference in their entirety.

What is claimed is:

1. A method of making a gold nanoparticle conjugate comprising:

contacting a trithiocarbonate of the following formula

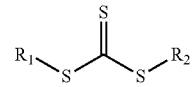

with an alkene of the following formula

to produce a polymer of the following formula

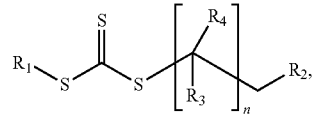

and contacting the polymer with a gold nanoparticle to form the gold nanoparticle conjugate, wherein at least one of contacting the trithiocarbonate and the alkene and contacting the polymer and the gold nanoparticle is performed under non-reducing conditions, and $R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

2. The method of claim 1, wherein the gold nanoparticle conjugate has the following formula

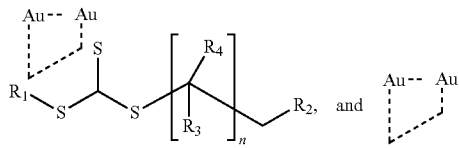

represents the surface of the gold nanoparticle.

3. The method of claim 1, wherein the trithiocarbonate and alkene are contacted under non-reducing conditions.

4. The method of claim 1, wherein the polymer and gold nanoparticle are contacted under non-reducing conditions.

5. The method of claim 1, wherein the polymer and gold nanoparticle are associated through more than one sulfur atom.

6. The method of claim 1, wherein the gold nanoparticle conjugate further comprises a functional group.

7. The method of claim 6, wherein the functional group is selected from the group consisting of carboxylic acids and carboxylic acid salt derivatives, acid halides,sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives.

8. The method of claim 1, wherein the gold nanoparticle conjugate further comprises a therapeutic agent covalently bonded to the polymer.

9. The method of claim 1, wherein the gold nanoparticle conjugate further comprises a targeting agent covalently bonded to the polymer.

10. A method of making a gold nanoparticle conjugate comprising:
contacting a compound of the following formula

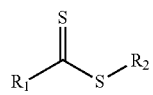

with an alkene of the following formula

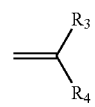

to produce a polymer of the following formula

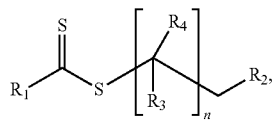

and
contacting the polymer with a gold nanoparticle to form the gold nanoparticle conjugate,
wherein at least one of contacting the compound and the alkene and contacting the polymer and the gold nanoparticle is performed under non-reducing conditions, and
$R_1$, $R_2$, $R_3$, and $R_4$ are each independently selected from hydrogen, alkyl, substituted alkyl, alkoxy, substituted alkoxy, acyl, substituted acyl, acylamino, substituted acylamino, alkylamino, substituted alkylamino, alkylsulfinyl, substituted alkylsulfinyl, alkylsulfonyl, substituted alkylsulfonyl, alkylthio, substituted alkylthio, alkoxycarbonyl, substituted alkoxycarbonyl, aryl, substituted aryl, arylalkyl, substituted arylalkyl, aryloxy, substituted aryloxy, aryloxycarbonyl, substituted aryloxycarbonyl, carbamoyl, substituted carbamoyl, cycloalkyl, substituted cycloalkyl, cycloheteroalkyl, substituted cycloheteroalkyl, dialkylamino, substituted dialkylamino, halo, heteroalkyl, substituted heteroalkyl, heteroaryl, substituted heteroaryl, heteroarylalkyl, substituted heteroarylalkyl, heteroalkyloxy, substituted heteroalkyloxy, heteroaryloxy and substituted heteroaryloxy.

11. The method of claim 10, wherein the compound is a dithioester, xanthate, or dithiocarbamate.

12. The method of claim 10, wherein the gold nanoparticle conjugate has the following formula

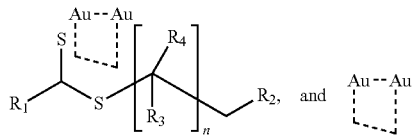

represents the surface of the gold nanoparticle.

13. The method of claim 10, wherein the compound and alkene are contacted under non-reducing conditions.

14. The method of claim 10, wherein the polymer and gold nanoparticle are contacted under non-reducing conditions.

15. The method of claim 10, wherein the polymer and gold nanoparticle are associated through more than one sulfur atom.

16. The method of claim 10, wherein the gold nanoparticle conjugate further comprises a functional group.

17. The method of claim 16, wherein the functional group is selected from the group consisting of carboxylic acids and carboxylic acid salt derivatives, acid halides, sulfonic acids and sulfonic acid salts, anhydride derivatives, hydroxyl derivatives, amine and amide derivatives, silane derivations, phosphate derivatives, nitro derivatives, succinimide and sulfo-containing succinimide derivatives, halide derivatives, alkene derivatives, morpholine derivatives, cyano derivatives, epoxide derivatives, ester derivatives, carbazole derivatives, azide derivatives, alkyne derivatives, acid containing sugar derivatives, glycerol analogue derivatives, maleimide derivatives, protected acids and alcohols, and acid halide derivatives.

18. The method of claim 10, wherein the gold nanoparticle conjugate further comprises a therapeutic agent covalently bonded to said polymer.

19. The method of claim 10, wherein the gold nanoparticle conjugate further comprises a targeting agent covalently bonded to said polymer.

* * * * *